United States Patent
Hossainy et al.

(10) Patent No.: US 8,053,019 B2
(45) Date of Patent: Nov. 8, 2011

(54) THERMAL TREATMENT OF A DRUG ELUTING IMPLANTABLE MEDICAL DEVICE

(75) Inventors: Syed F. A. Hossainy, Fremont, CA (US);
Fuh-Wei Tang, Temecula, CA (US);
Stephen D. Pacetti, San Jose, CA (US);
Jeff Royal, San Francisco, CA (US);
Dorie M. Happ, San Jose, CA (US);
Kurt Scheinpflug, Sunnyvale, CA (US);
Ty Hu, Pembroke Pines, FL (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/699,127

(22) Filed: Feb. 3, 2010

(65) Prior Publication Data
US 2010/0136213 A1    Jun. 3, 2010

Related U.S. Application Data

(60) Division of application No. 10/603,794, filed on Jun. 25, 2003, now Pat. No. 7,682,647, which is a continuation-in-part of application No. 10/108,004, filed on Mar. 27, 2002, and a continuation-in-part of application No. 10/304,360, filed on Nov. 25, 2002, now abandoned, which is a division of application No. 09/751,691, filed on Dec. 28, 2000, now Pat. No. 6,503,556, said application No. 10/603,794 is a continuation-in-part of application No. 09/750,595, filed on Dec. 28, 2000, now Pat. No. 6,790,228, which is a continuation-in-part of application No. 09/470,559, filed on Dec. 23, 1999, now Pat. No. 6,713,119, which is a continuation-in-part of application No. 09/390,855, filed on Sep. 3, 1999, now Pat. No. 6,287,628, and a continuation-in-part of application No. 09/390,069, filed on Sep. 3, 1999, now Pat. No. 6,379,381, said application No. 09/750,595 is a continuation-in-part of application No. 09/715,510, filed on Nov. 17, 2000, now Pat. No. 6,749,626, which is a continuation-in-part of application No. 09/540,241, filed on Mar. 31, 2000, now abandoned.

(51) Int. Cl.
*B05D 3/02* (2006.01)
*A61F 2/06* (2006.01)
*A61L 33/00* (2006.01)

(52) U.S. Cl. .... 427/2.24; 427/2.1; 427/2.25; 427/372.2; 623/1.11; 623/1.42; 623/1.46

(58) Field of Classification Search ........... 427/2.1, 427/2.24, 2.25, 372.2; 623/1.11, 1.42, 1.46
See application file for complete search history.

(56) References Cited

U.S. PATENT DOCUMENTS 5,468,253 A * 11/1995 Bezwada et al. .......... 606/230
(Continued)

FOREIGN PATENT DOCUMENTS

WO    WO 02/058753    8/2002
(Continued)

OTHER PUBLICATIONS

EPO Search Report for 05780079.9-2107, mailed Jan. 17, 2008, 6 pgs.

(Continued)

*Primary Examiner* — Timothy Meeks
*Assistant Examiner* — Cachet Sellman
(74) *Attorney, Agent, or Firm* — Squire Sanders & Dempsey, (US) LLP

(57) ABSTRACT

A coating and a method of coating an implantable medical device, such as a stent, is disclosed. The method includes subjecting the coating to a thermal condition such as a temperature above the glass transition temperature of a polymer included in the coating.

19 Claims, 6 Drawing Sheets

U.S. PATENT DOCUMENTS

| | | | |
|---|---|---|---|
| 5,651,174 | A | 7/1997 | Schwartz et al. |
| 5,795,318 | A | 8/1998 | Wang et al. |
| 5,824,048 | A * | 10/1998 | Tuch .............................. 128/898 |
| 5,961,914 | A | 10/1999 | Mannion et al. |
| 5,968,091 | A | 10/1999 | Pinchuk |
| 6,056,906 | A | 5/2000 | Werneth et al. |
| 6,066,156 | A | 5/2000 | Yan |
| 6,100,346 | A | 8/2000 | Jamiolkowski et al. |
| 6,153,252 | A * | 11/2000 | Hossainy et al. .............. 427/2.3 |
| 6,221,102 | B1 | 4/2001 | Baker et al. |
| 6,293,959 | B1 | 9/2001 | Miller et al. |
| 6,309,402 | B1 | 10/2001 | Jendersee et al. |
| 6,395,326 | B1 | 5/2002 | Castro et al. |
| 6,406,739 | B1 | 6/2002 | LeBoeuf et al. |
| 6,451,373 | B1 | 9/2002 | Hossainy et al. |
| 6,574,497 | B1 | 6/2003 | Pacetti |
| 6,652,581 | B1 | 11/2003 | Ding |
| 6,739,033 | B2 | 5/2004 | Hijlkema et al. |
| 6,823,576 | B2 | 11/2004 | Austin |
| 6,948,223 | B2 | 9/2005 | Shortt |
| 7,077,859 | B2 | 7/2006 | Sirhan et al. |
| 7,291,165 | B2 | 11/2007 | Rosenthal et al. |
| 2004/0220665 | A1 | 11/2004 | Hossainy et al. |
| 2005/0118344 | A1 | 6/2005 | Pacetti |
| 2005/0119720 | A1 | 6/2005 | Gale et al. |
| 2005/0233062 | A1 | 10/2005 | Hossainy et al. |

FOREIGN PATENT DOCUMENTS

| | | |
|---|---|---|
| WO | WO 03/035131 | 5/2003 |
| WO | WO 03/082368 | 10/2003 |
| WO | WO 2005/004945 | 1/2005 |

OTHER PUBLICATIONS

EPO Examination Report for application 04 812 597.5-2307, mailed Feb. 26, 2007, 2 pgs.
EPO Examination Report for application 04 812 597.5-2307, mailed Sep. 6, 2007, 3 pgs.
EPO Examination Report for application 04 812 597.5-2307, mailed Jul. 4, 2008, 3 pgs.
International Search Report and Written Opinion for PCT/US2004/017060, filed May 28, 2004, mailed Dec. 30, 2004, 10 pgs.
International Search Report and Written Opinion for PCT/US2004/040121, filed Nov. 30, 2004, mailed Apr. 12, 2005, 12 pgs.
Perego et al., "Copolymers of L and D, L Lactide with 6-caprolactone:synthesis and characterization", Macromol. Chem. 194, pp. 2463-2469 (1993).

* cited by examiner

THERMAL TREATMENT OF A DRUG ELUTING IMPLANTABLE MEDICAL DEVICE

CROSS REFERENCE

This application is a divisional of application Ser. No. 10/603,794, filed on Jun. 25, 2003, (U.S. Pat. No. 7,682,647); and application Ser. No. 10/603,794 is a continuation-in-part of application Ser. No. 10/108,004, filed on Mar. 27, 2002 (U.S. Patent Application Publication No. US 2007-0032853 A1 ), and is a continuation-in-part of application Ser. No. 10/304,360, filed on Nov. 25, 2002 (abandoned), which is a divisional of application Ser. No. 09/751,691, filed on Dec. 28, 2000, (U.S. Pat. No. 6,503,556); application Ser. No. 10/603,794 is also a continuation-in-part of application Ser. No. 09/750,595, filed on Dec. 28, 2000, (U.S. Pat. No. 6,790,228), which is a continuation-in-part of application Ser. No. 09/470,559, filed on Dec. 23, 1999, (U.S. Pat. No. 6,713,119), which is a continuation-in-part of application Ser. No. 09/390,855, filed on Sep. 3, 1999, (U.S. Pat. No. 6,287,628), and a continuation-in-part of application Ser. No. 09/390,069, filed on Sep. 3, 1999 (U.S. Pat. No. 6,379,381); and said application Ser. No. 09/750,595 is also a continuation-in-part of application Ser. No. 09/715,510, filed on Nov. 17, 2000 (U.S. Pat. No. 6,749,626), which is a continuation-in-part of application Ser. No. 09/540,241, filed on Mar. 31, 2000 (abandoned).

BACKGROUND OF THE INVENTION

1. Field of the Invention

The invention relates to drug eluting implantable medical devices, one example of which is a stent. More particularly, the invention relates to a method of thermally treating a drug eluting implantable medical device.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to remodel the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis a stent is implanted in the lumen to maintain the vascular patency.

Stents act as scaffoldings, functioning to physically hold open and, if desired, to expand the wall of the passageway. Typically, stents are capable of being compressed so that they can be inserted through small lumens via catheters and then expanded to a larger diameter once they are at the desired location. Mechanical intervention via stents has reduced the rate of restenosis as compared to balloon angioplasty. Yet, restenosis is still a significant clinical problem with rates ranging from 20-40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method of medicating stents involves the use of a polymeric carrier coated onto the surface of the stent. A composition including a solvent, a polymer dissolved in the solvent, and an active agent dispersed in the blend is applied to the stent by immersing the stent in the composition or by spraying the composition onto the stent. The solvent is allowed to evaporate, leaving on the stent strut surfaces a coating of the polymer and the active agent impregnated in the polymer.

A potential shortcoming of the foregoing method of medicating stents is that the release rate of the active agent may be too high to provide an efficacious treatment. This shortcoming may be especially pronounced with certain active agents. For instance, it has been found that the release rate of 40-O-(2-hydroxy)ethyl-rapamycin from a standard polymeric coating is greater than 50% in about 24 hours. Thus, there is a need for a coating that reduces the release rate of active agents in order to provide a more efficacious release rate profile.

Another shortcoming of the foregoing method of medicating stents is that there can be significant manufacturing inconsistencies. For instance, there can be release rate variability among different stents. It is believed that when some polymers dry on a stent surface to form a coating, different polymer morphologies can develop for different stent coatings, even if the coating process parameters are consistent. The differences in polymer morphology may cause the release rate of the active agent from the polymeric coatings to vary significantly. As a consequence of the inconsistent release rate profiles among stents, there can be clinical complications. Additionally, when stents are stored, the release rate from the stent coating can change during the storage time, known as "release rate drift." Thus, there is a need for a method that reduces the variability of the release rate of active agents among stents and over time. The present invention provides a method and coating to meet the foregoing as well as other needs.

SUMMARY

In accordance with one aspect of the invention, a method of manufacturing an implantable medical device is disclosed including exposing a dry coating on the device to a temperature greater than ambient temperature for a duration of time, the dry coating comprising a polymer, an active agent, and less than about 2% residual fluid content (w/w), wherein the duration of exposure is sufficient to decrease the release rate of the active agent from the coating after the coating has been implanted into a biological lumen. In one embodiment, the dry coating comprises a reservoir layer having the active agent, and a primer layer disposed under a portion of the reservoir layer. In another embodiment, the dry coating comprises a reservoir layer having the active agent, and a barrier layer covering a portion of the reservoir layer. The polymer comprises, in yet another embodiment, an ethylene vinyl alcohol copolymer, an ethylene-vinyl acetate copolymer, poly(butylmethacrylate), or a combination of the same. In another embodiment, the active agent is rapamycin, 40-O-(2-hydroxy)ethyl-rapamycin, or a functional analog or structural derivative thereof. In a further embodiment, the standard deviation of the mean release rate of the active agent in a 24 hour period is lower than the standard deviation of the mean release rate for a group of devices which have not been exposed to the temperature.

In accordance with a further aspect of the present invention, a method of manufacturing a drug eluting stent is disclosed including applying a composition to a stent, the composition including a polymer and a solvent; allowing the solvent to evaporate to form a coating; and exposing the coating to a temperature equal to or greater than the glass transition temperature of the polymer for a duration of time. In one embodiment, the composition further includes an active agent. In another embodiment, the solvent is allowed to evaporate to form a dry coating comprising less than about 2% residual fluid content (w/w). In another embodiment, the temperature is equal to the glass transition temperature of the polymer plus the melting temperature of the polymer, divided by 2. In a further embodiment, the polymer is a blend of two or more polymers.

In another aspect of the present invention, a method of manufacturing a drug eluting stent is disclosed including applying a composition to a stent, the composition including a semicrystalline polymer, an active agent and a solvent; allowing the solvent to evaporate to form a dry coating, the dry coating comprising less than about 2% residual fluid content (w/w); and exposing the dry coating to the crystallization temperature of the polymer for a duration of time.

In a further aspect, a method of manufacturing a drug eluting stent is disclosed including forming a dry polymeric coating on a stent having less than about 2% residual fluid content (w/w), the dry polymeric coating comprising a reservoir layer including a polymer and an active agent, and a barrier layer including a polymer covering a portion of the reservoir layer; and exposing the polymer included in the barrier layer to a temperature equal to or greater than the glass transition temperature of the polymer. In one embodiment, the glass transition temperature of the polymer included in the barrier layer is lower than the glass transition temperature of the polymer included in the reservoir layer.

In another aspect of the present invention, a method of manufacturing a drug eluting stent is disclosed, including forming a polymeric coating on a stent, the polymeric coating comprising a reservoir layer including a semicrystalline polymer and an active agent; and exposing the polymer included in the reservoir layer to the crystallization temperature of the polymer. In a further aspect, a method of manufacturing a drug eluting stent is disclosed, including forming a polymeric coating on a stent, the polymeric coating comprising a reservoir layer including a polymer and an active agent, and a barrier layer including a semicrystalline polymer covering a portion of the reservoir layer; and exposing the polymer included in the barrier layer to the crystallization temperature of the polymer.

In yet another aspect, a method of coating an implantable medical device is disclosed, including applying a composition to an implantable medical device, the composition comprising a polymer dissolved in a solvent; and heating the composition to a temperature equal to or greater than the glass transition temperature of the polymer. In one embodiment, the composition is heated to the temperature until a dry coating is formed on the device, the coating comprising less than about 2% residual solvent (w/w). In one embodiment, the composition is substantially free of any active agents. In yet another embodiment, the composition further comprises an active agent.

DETAILED DESCRIPTION

Coating

Herein is disclosed a method of manufacturing a drug eluting implantable device, such as a stent, by using a thermal treatment process. The method includes exposing (i.e., heating) a polymeric drug coating to a temperature sufficient to reduce the release rate of the drug from the coating. The coating can include one or more active agents dispersed within one or more polymers. The active agent can be any substance capable of exerting a therapeutic or prophylactic effect. "Polymer," "poly," and "polymeric" are inclusive of homopolymers, copolymers, terpolymers etc., including random, alternating, block, cross-linked, blends and graft variations thereof.

Some of embodiments of the polymeric coating are illustrated by FIGS. 1A-1E. The Figures have not been drawn to scale, and the thickness of the various layers have been over or under emphasized for illustrative purposes.

Figure 1A:
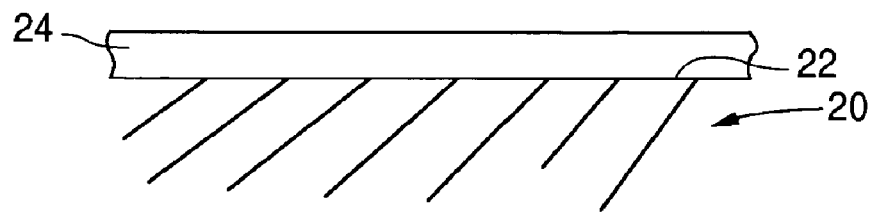
FIGS. 1A-1E illustrate coatings deposited over an implantable medical substrate in accordance with various embodiments of the present invention.

Referring to FIG. 1A, a body of a medical substrate 20, such as a stent, is illustrated having a surface 22. A reservoir layer 24 having a polymer and an active agent (e.g., 40-O-(2-hydroxy)ethyl-rapamycin) dispersed in the polymer is deposited on surface 22. The polymer in reservoir layer 24 can be a homopolymer, copolymer, terpolymer, etc. and can include random, alternating, block, cross-linked, blends and graft variations thereof. Reservoir layer 24 can release the active agent when medical substrate 20 is inserted into a biological lumen.

Figure 1B:
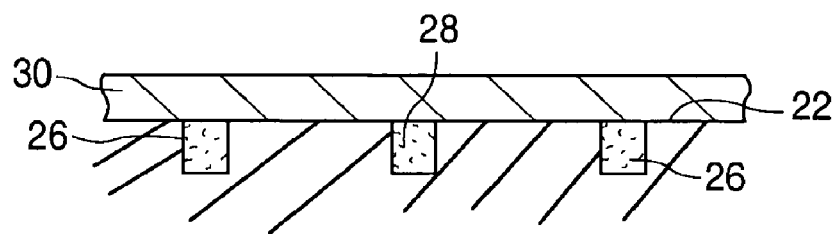

Referring to FIG. 1B, medical substrate 20 includes cavities or micro-pores 26 formed in the body for releasably containing an active agent, as illustrated by dotted region 28. A barrier layer or rate-reducing membrane 30 including a polymer is disposed on surface 22 of medical substrate 20, covering cavities 26. Barrier layer 30 functions to reduce the rate of release of an active agent from medical substrate 20.

Figure 1C:
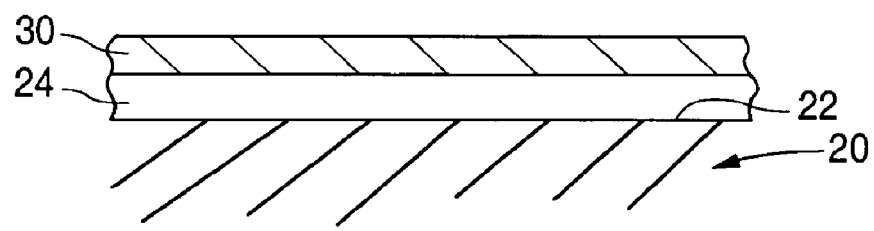

Referring to FIG. 1C, medical substrate 20 is illustrated having active-agent-containing or reservoir layer 24 deposited on surface 22. Barrier layer 30 is formed over at least a selected portion of reservoir layer 24

Figure 1D:
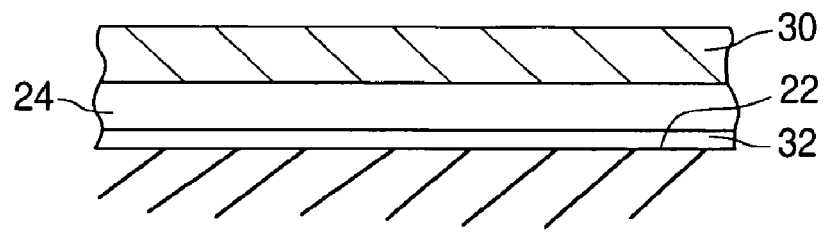

Referring to FIG. 1D, reservoir coating 24 is deposited on a primer layer 32. Barrier layer 30 is formed over at least a portion of reservoir layer 24. Primer layer 32 serves as an intermediary layer for increasing the adhesion between reservoir layer 24 and surface 22. Increasing the amount of active agent admixed within the polymer can diminish the adhesiveness of reservoir layer 24 to surface 22. Accordingly, using an active agent-free polymer as an intermediary primer layer 32 allows for a higher active agent content for reservoir layer 24.

Figure 1E:
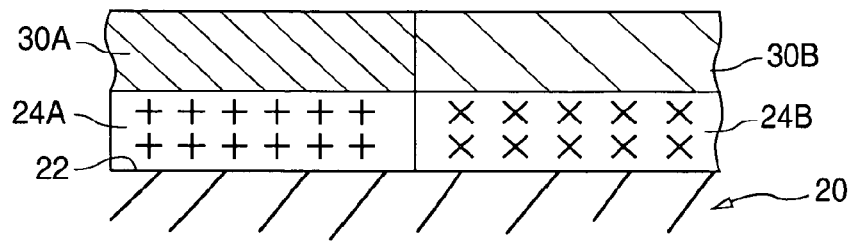

FIG. 1E illustrates medical substrate 20 having a first reservoir layer 24A disposed on a selected portion of surface 22 of medical substrate 20. First reservoir layer 24A contains a first active agent, e.g., 40-O-(2-hydroxy)ethyl-rapamycin. A second reservoir layer 24B can also be disposed on surface 22. Second reservoir layer 24B contains a second active agent, e.g., taxol. First and second reservoir layers 24A and 24B are covered by first and second barrier layers 30A and 30B, respectively. One of ordinary skill in the art can appreciate that barrier layer 30 can be deposited only on selected areas of reservoir layer 24 so as to provide a variety of selected release parameters. Such selected patterns may become particularly useful if a combination of active agents are used, each of which requires a different release parameter.

By way of example, and not limitation, the impregnated reservoir layer 24 can have a thickness of about 0.1 microns to about 10 microns, more narrowly about 0.5 microns to 2 microns. The particular thickness of reservoir layer 24 is based on the type of procedure for which medical substrate 20 is employed and the amount of the active agent to be delivered. The amount of the active agent to be included on medical substrate 20 can be further increased by applying a plurality of reservoir layers 24 on top of one another. Barrier layer 30 can have any suitable thickness, as the thickness of barrier layer 30 is dependent on parameters such as, but not limited to, the desired rate of release and the procedure for which the stent will be used. For example, barrier layer 30 can have a thickness of about 0.1 to about 10 microns, more narrowly from about 0.25 to about 5 microns. Primer layer 32 can have any suitable thickness, examples of which can be in the range of about 0.1 to about 10 microns, more narrowly about 0.1 to about 2 microns.

Thermal Treatment of the Coating

The implantable medical device manufactured in accordance with embodiments of the present invention may be any suitable medical substrate that can be implanted in a human or veterinary patient. In the interests of brevity, methods of manufacturing a drug eluting stent are described herein. However, one of ordinary skill in the art will understand that other medical substrates can be manufactured using the methods of the present invention.

As noted above, the method of the present invention includes exposing a polymeric drug coating to a temperature sufficient to reduce the release rate of the drug from the coating. A stent having a polymeric drug coating can be provided for the thermal treatment process. Alternatively, the polymeric drug coating can be formed on the stent surface as described in further detail herein.

In one embodiment of the present invention, the polymeric coating is a dry coating. "Dry coating" is defined as a coating with less than about 10% residual fluid (e.g., solvent(s) or water) content (w/w). In one embodiment, the coating has less than about 2% residual fluid content (w/w), and more narrowly, less than about 1% residual fluid content (w/w). The amount of residual fluids in the coating can be determined by a Karl Fisher, or ThermoGravimetric Analysis (TGA), study. For example, a coated stent can be placed in the TGA instrument, and the weight change can be measured at 100° C. as an indication of water content, or measured at a temperature equal to the boiling temperature of the solvent used in the coating as an indication of the solvent content.

The thermal treatment process can be conducted immediately after the composition has been applied to the stent. Alternatively, the coating can be subjected to the thermal treatment process after a dry polymeric drug coating has been formed on a stent. The stent can undergo the thermal treatment process at any appropriate stage of manufacture, such as before being packaged, or while the stent is being secured onto a stent delivery device such as a catheter. In other words, for the later option, the stent coating can be exposed to the appropriate temperature as the stent is being crimped onto the delivery device.

The heat source/emitter used to thermally treat the coating can be any apparatus that emits radiation capable of heating the polymeric coating. For example, the heat source can be a cauterizer tip, a RF source, or a microwave emitter. The heat source can also be a blower that includes a heating device so that the blower can direct a warm gas (e.g., air, argon, nitrogen, etc.) onto the implantable device. For example, the heating device can be an electric heater incorporating heating coils or a system that includes a gas source and a computer controller to control the temperature of the gas directed at the stents.

Figure 2:
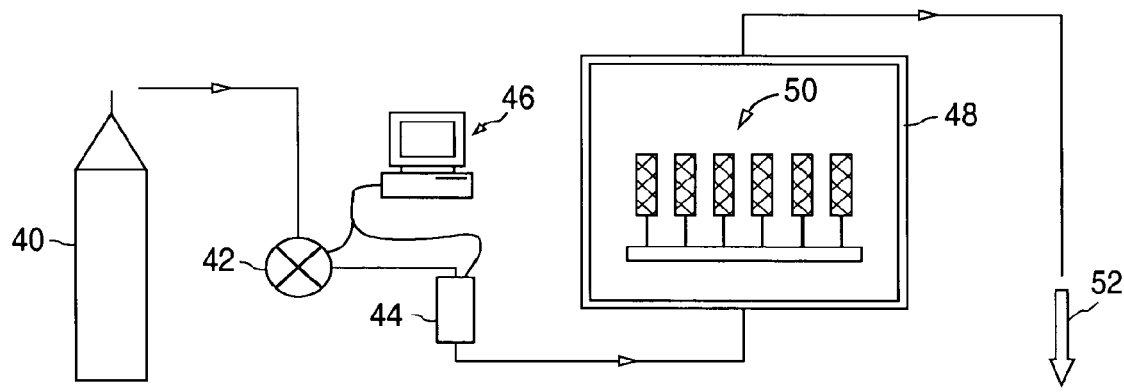
FIG. 2 is an illustration of a system for thermally treating drug eluting stents.

Referring to FIG. 2, a gas system for the thermal treatment process can include a gas source 40, a flow controller 42 (e.g., a flow controller available from Eurotherm Control, Inc., Leesburg, Va.), an in-line heater 44 (e.g., an in-line heater available from Sylvania, Danvers, Mass.), a computer controller 46, an air tight chamber 48 for holding a plurality of stents 50 and an exhaust 52. Computer controller 46 can be in communication with flow controller 42 and in-line heater 44 to control the amount of air and temperature, respectively, that is delivered to chamber 48. Exhaust 52 can provide a route for unwanted components (e.g., oxygen) to travel after being removed from the stent coatings. In-line heater 44 can be used to precisely and gradually increase the temperature of the gas delivered by gas source 40 to the temperature used to conduct the thermal treatment.

The thermal treatment can be beneficial because, without thermal treatment, the active agent (e.g., 40-O-(2-hydroxy)ethyl-rapamycin) can diffuse from the polymer matrix at a rate that could be too high for certain clinical conditions. For example, by using the process of the present invention, the coating can be exposed to a sufficient temperature effective to decrease the release rate of 40-O-(2-hydroxy)ethyl-rapamycin, or analog or derivative thereof, by about 50% as compared to a control group, as demonstrated in Example 17 below.

Additionally, the thermal treatment process of the present invention can increase the manufacturing consistency of drug eluting stents by reducing the variability of the release rate of active agents among stents. The thermal treatment process can also reduce the release rate drift over time. "Release rate drift" refers to the phenomenon in which the release rate of an active agent from a polymeric coating can change over time, for instance while the stent is in storage. Release rate drift may occur because of changes in the morphology of a polymeric coating over a period of time, for example if the polymeric coating is exposed to degradation agents such as oxygen and moisture. As demonstrated by Example 59, by exposing a stent coating to a temperature greater than the glass transition temperature of the polymer in the coating, the standard deviation of the mean release rate of the active agent in a 24 hour period can be decreased so that the standard deviation is lower than the standard deviation of the mean release rate for a baseline group of stents (i.e., stents which have not been subjected to a thermal treatment process). It is believed that the thermal treatment process can increase manufacturing consistency by moving a polymeric stent coating closer to a thermodynamic equilibrium.

In one embodiment of the present invention, a polymeric coating having an active agent is exposed to a temperature greater than ambient temperature that is sufficient to decrease the release rate of the active agent from the coating. For example, the coatings illustrated in FIGS. 1A-1E can be exposed to the thermal treatment process to decrease the release rate of the active agent from the coatings. Without being bound by any particular theory, it is believed that the thermal treatment process of the present invention can decrease the release rate of the active agent from the polymeric drug coating by redistributing the microphase distribution of the active agent in the coating by causing the active agent to cluster. In particular, the redistribution can decrease the surface area of the active agent clusters as the clusters are exposed to the fluid at the treatment site. Furthermore, the thermal treatment can decrease the release rate of the active agent by (1) decreasing the free volume in an amorphous polymer; (2) increasing the crosslinking of the polymer in the coating; and (3) repairing minute imperfections in the coating such as cracks formed during the initial coating process.

In another embodiment of the present invention, the polymer in the coating is a semicrystalline polymer (e.g., polyvinyl chloride or an ethylene vinyl alcohol copolymer), and the polymeric coating is exposed to the crystallization temperature ($T_c$) of the polymer. In one embodiment, the $T_c$ of the polymer is greater than ambient temperature. "Crystallization temperature" refers to the temperature at which a semicrystalline polymer has its highest percent crystallinity. Amorphous polymers do not exhibit a crystallization temperature. Methods of determining a crystallization temperature are described below. The crystallization temperature of ethylene vinyl alcohol copolymer (44 mole % ethylene), for instance, is about 415° K (ethylene vinyl alcohol copolymer ("EVAL") is commonly known by the generic name EVOH or by the trade name EVAL). Other examples of crystallization temperatures include 396° K for poly(ethylene terephthalate) as measured by differential scanning calorimetry (as reported by Parravicini et al., J. Appl. Polym. Sci., 52(7), 875-85 (1994)); and 400° K for poly(p-phenylene sulfide) as measured by differential scanning calorimetry (as reported by Ding, et al. Macromolecules, 29(13), 4811-12 (1996)).

It is believed that an active agent has a greater diffusivity in the amorphous domain of a polymer as compared to the crystalline domain. Most polymeric materials used for drug eluting stent coatings have some crystallinity and the degree of polymer crystallinity directly affects an active agent's diffusivity due to changes in free volume and the increase in the volume fraction of the crystalline phase. It is further believed that the composition components (e.g., solvents) and process parameters that are often used to coat stents do not allow for maximum crystallinity in the polymer matrix. If a highly volatile solvent is included in the composition, for example, then the polymer does not have sufficient time to fully crystallize before the solvent has evaporated from the coating.

Without being bound by any particular theory, it is believed that the diffusion rate of the active agent from the polymer can be decreased because heating the polymer increases the percent crystallinity of the polymer. "Percent crystallinity" refers to the percentage of the polymer material that is in a crystalline form. In one embodiment of the present invention, the polymer is a semicrystalline polymer having between 40 and 75 percent crystallinity (e.g., poly(vinylidene fluoride achieving about a 65 percent crystallinity and poly(6-aminocaproic acid) achieving about a 64 percent crystallinity). The methods of the present invention can increase the percent crystallinity of the polymer by about 5 to 30, more narrowly about 20 to 30 percent crystallinity.

Those of ordinary skill in the art understand that there are several methods for determining the percent crystallinity in polymers. These methods are, for example, described in L. H. Sperline, Introduction to Physical Polymer Science (3rd ed. 2001). The first involves the determination of the heat of fusion of the whole sample by calorimetric methods. The heat of fusion per mole of crystalline material can then be estimated independently by melting point depression experiments. The percent crystallinity is then given by heat of fusion of the whole sample divided by the heat of fusion per mole of crystalline material times 100.

A second method involves the determination of the density of the crystalline portion via X-ray analysis of the crystal structure, and determining the theoretical density of a 100% crystalline material. The density of the amorphous material can be determined from an extrapolation of the density from the melt to the temperature of interest. Then the percent crystallinity is given by:

$$\% \text{ Crystallinity} = \frac{\rho_{exptl} - \rho_{amorph}}{\rho_{100\% \ cryst} - \rho_{amorph}} \times 100$$

where $\rho_{exptl}$ represents the experimental density, and $\rho_{amorph}$ and $\rho_{100\% \ cryst}$ are the densities of the amorphous and crystalline portions, respectively.

A third method stems from the fact that X-ray diffraction depends on the number of electrons involved and is thus proportional to the density. Besides Bragg diffraction lines for the crystalline portion, there is an amorphous halo caused by the amorphous portion of the polymer. The amorphous halo occurs at a slightly smaller angle than the corresponding crystalline peak, because the atomic spacings are larger. The amorphous halo is broader than the corresponding crystalline peak, because of the molecular disorder. This third method can be quantified by the crystallinity index, CI, where $$CI = \frac{A_c}{A_a + A_c}.$$

and where $A_c$ and $A_a$ represent the area under the Bragg diffraction line and corresponding amorphous halo, respectively.

In another embodiment of the present invention, the thermal treatment process can be used to heat a polymeric coating on a stent to a temperature equal to or greater than the glass transition temperature ($T_g$) of the polymer. Alternatively, in another embodiment, the coating can including an active agent and be subjected to a thermal treatment by exposing the coating to a temperature equal to or greater than the $T_g$ of the polymer in the coating to reduce the release rate of the active agent. In one embodiment, the $T_g$ and $T_m$ of the polymer is greater than ambient temperature. Both amorphous and semicrystalline polymers exhibit glass transition temperatures.

Additionally, if the polymer is a semicrystalline polymer, the dry polymeric coating can be exposed to a temperature equal to or greater than the $T_g$ and less than the melting temperature ($T_m$) of the polymer in the coating. Amorphous polymers do not exhibit a $T_m$.

In yet another embodiment, if the polymer is a semicrystalline polymer, the polymeric coating is exposed to the annealing temperature of the polymer. "Annealing temperature" refers to the temperature equal to $(T_g+T_m)/2$. The annealing temperature for EVAL, for instance, is about 383° K. The polymeric coating can also be exposed, in another embodiment, to a temperature equal to 0.9 times the melting temperature of the polymer, with the melting temperature expressed in Kelvin (e.g., about 394° K for EVAL).

The $T_g$ is the temperature at which the amorphous domains of a polymer change from a brittle vitreous state to a plastic state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement.

Figure 4:
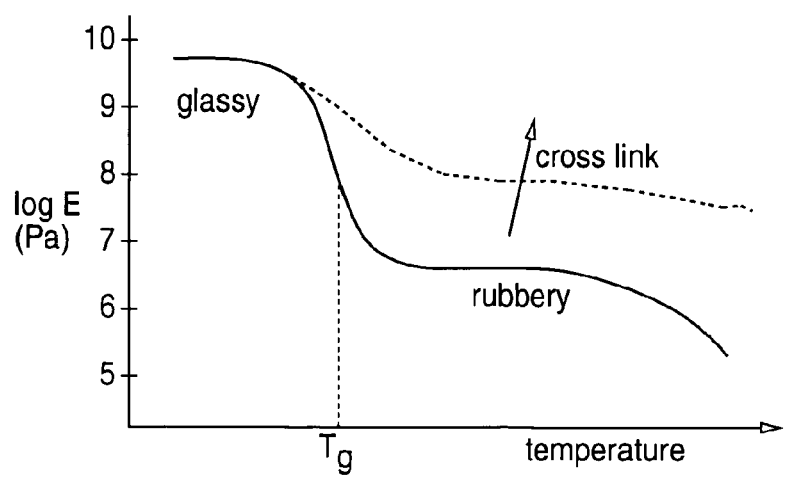
FIG. 4 is graph of the relationship of elasticity versus temperature for a polymer.

$T_g$ of a given polymer can be dependent on the heating rate and can be influenced by the thermal history of the polymer. Furthermore, the chemical structure of the polymer heavily influences the glass transition by affecting mobility. Generally, flexible main-chain components lower the $T_g$; bulky side-groups raise the $T_g$; increasing the length of flexible side-groups lowers the $T_g$; and increasing main-chain polarity increases the $T_g$. Additionally, the presence of crosslinking polymeric components can increase the observed $T_g$ for a given polymer. For instance, FIG. 4 illustrates the effect of temperature and crosslinking on the modulus of elasticity of a polymer, showing that forming cross-links in a polymer can increase the $T_g$ and shift the elastic response to a higher plateau—one that indicates that the polymer has become more glassy and brittle. Moreover, molecular weight can significantly influence $T_g$, especially at lower molecular weights where the excess of free volume associated with chain ends is significant.

The $T_m$ of a polymer, on the other hand, is the temperature at which the last trace of crystallinity in a polymer disappears as a sample is exposed to increasing heat. The $T_m$ of a polymer is also know as the fusion temperature ($T_f$). The $T_m$ is always greater than the $T_g$ for a given polymer.

Like the $T_g$, the melting temperature of a given polymer is influenced by the structure of the polymer. The most influential inter- and intramolecular structural characteristics include structural regularity, bond flexibility, close-packing ability, and interchain attraction. In general, high melting points are associated with highly regular structures, rigid molecules, close-packing capability, strong interchain attraction, or two or more of these factors combined.

Figure 3:
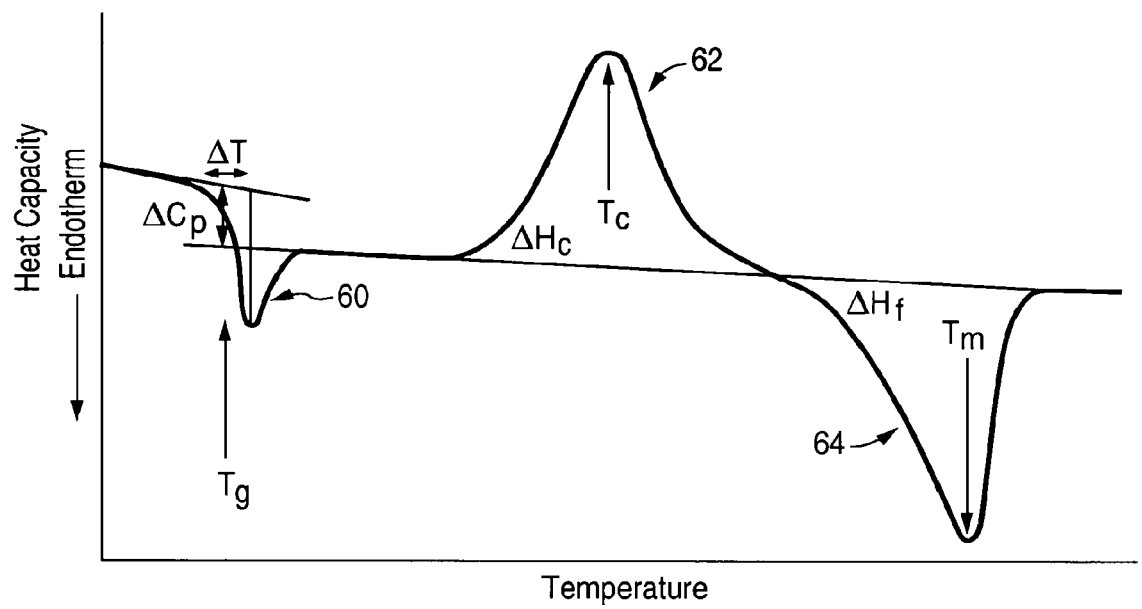
FIG. 3 is a graph of the relationship of heat capacity versus temperature for a polymer.

Referring to FIG. 3, if the coating polymer is a semicrystalline polymer, as the polymeric coating is exposed to an increasing temperature, the polymer exhibits three characteristic thermal transitions represented by first curve 60, second curve 62 and third curve 64. FIG. 3 illustrates the change in heat capacity (endothermic v. exothermic) of a semicrystalline polymer as the polymer is exposed to an increasing temperature, as measured by the differential scanning calorimetry (DSC) method. DSC uses the relationship between heat capacity and temperature as the basis for determining the thermal properties of polymers and is further described below.

By way of illustration, when a semicrystalline polymer is exposed to an increasing temperature, the crystallinity of the polymer begins to increase as the increasing temperature reaches the $T_g$. At and above the $T_g$, the increased molecular motion of the polymer allows the polymer chains to move around more to adopt a more thermodynamically stable relationship, and thereby increase the percent crystallinity of the polymer sample. In FIG. 3, the $T_g$ is shown as point $T_g$ of first curve 60, which is the temperature at which half of the increase in heat capacity ($\Delta C_p$) has occurred. The percent crystallinity then increases rapidly after point $T_g$ and is maximized at the $T_c$ of the polymer, which is indicated at the point $T_c$ (the apex of second curve 62). As the temperature continues to increase, the temperature approaches the melting temperature ($T_m$) of the polymer, and the percent crystallinity decreases until the temperature reaches the melting temperature of the polymer (at point $T_m$ of curve 64). As noted above, $T_m$ is the temperature where the last trace of crystallinity in the polymer disappears. The heat of crystallization, $\Delta H_c$, and the heat of fusion, $\Delta H_f$, can be calculated as the areas under curves 62 and 64. The heat of crystallization and heat of fusion must be equal, but with opposite signs.

The $T_g$ and/or the $T_m$ of the polymer that is to be exposed to the thermal treatment should be determined experimentally in order to determine which temperatures can be used to thermally treat the dry polymeric coating. As used herein, "test polymer" means the polymer that is measured to determine the $T_g$ and/or the $T_m$ of the polymer. "Coating polymer" means the polymer that is actually applied as a component of the stent coating.

In order to accurately characterize the thermal properties of the coating polymer, one should consider the number of factors that can influence the $T_g$ and $T_m$ of a polymer. In particular, the factors include (1) the structure of the polymer (e.g., modification of side groups and dissimilar stereoregularity); (2) the molecular weight of the polymer; (3) the molecular-weight distribution ($M_w/M_n$) of the polymer; (4) the crystallinity of the polymer; (5) the thermal history of the polymer; (6) additives or fillers that are included in the polymer; (7) the pressure applied to the polymer as the polymer is heated; (8) residual fluids in the polymer and (9) the rate that the polymer is heated.

One can account for the foregoing factors by using a test polymer that is substantially the same as the coating polymer, and is tested under substantially the same conditions as the conditions used to conduct the thermal treatment of the polymeric coating. The test polymer should have the same chemical structure as the coating polymer, and should have substantially the same molecular weight and molecular-weight distribution as the coating polymer. For example, if the polymer is a blend of copolymers or homopolymers, the test polymer should have substantially the same percentage of components as the coating polymer. At the same time, the test polymer should have substantially the same crystallinity as the coating polymer. Methods of determining cystallinity are discussed herein. Additionally, the composition used to form the test polymer should include the same compounds (e.g., additives such as therapeutic substances) and fluids (e.g., solvent(s) and water) that are mixed with the coating polymer. Moreover, the test polymer should have the same thermal history as the coating polymer. The test polymer should be prepared under the same conditions as the coating polymer, such as using the same solvent, temperature, humidity and mixing conditions. Finally, the heating rate used for measuring the transition temperature of the test polymer should be substantially similar to the heating rate used to conduct the thermal treatment of the polymeric coating.

The $T_g$ and $T_m$ of the test polymer can be measured experimentally by testing a bulk sample of the polymer. As understood by one of ordinary skill in the art, a bulk sample of the polymer can be prepared by standard techniques, for example those that are outlined in the documentation accompanying the instruments used to measure the transition temperature of the polymer.

There are several methods that can be used to measure the $T_g$ and $T_m$ of a polymer. The $T_g$ and $T_m$ can be observed experimentally by measuring any one of several basic thermodynamic, physical, mechanical, or electrical properties as a function of temperature. Methods of measuring glass transition temperatures and melting temperatures are understood by one of ordinary skill in the art and are discussed by, for example, L. H. Sperling, Introduction to Physical Polymer Science, Wiley-Interscience, New York (3rd ed. 2001), and R. F. Boyer, in Encyclopedia of Polymer Science and Technology, Suppl. Vol. 2, N. M. Bikales, ed., Interscience, New York (1977).

Figure 5:
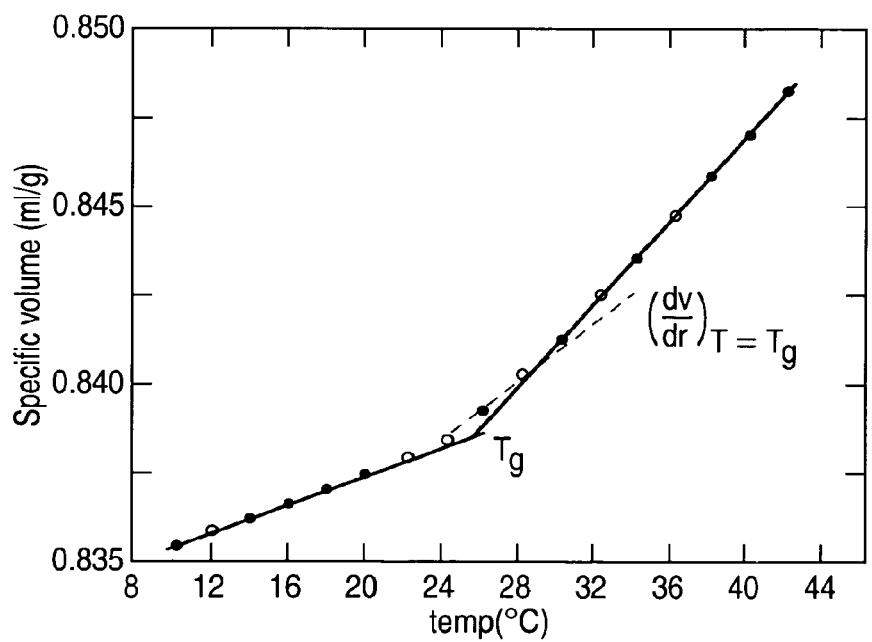
FIG. 5 is a graph of the relationship of specific volume versus temperature for a polymer.

The $T_g$ of a bulk sample can be observed by measuring the expansion of the polymer as the polymer is exposed to increasing temperature. This process is known as dilatometry. There are two ways of characterizing polymers via dilatometry. One way is to measure the linear expansivity of the polymer sample. Another method involves performing volume-temperature measurements, where the polymer is confined by a liquid and the change in volume is recorded as the temperature is raised. The usual confining liquid is mercury, since it does not swell organic polymers and has no transition of its own through most of the temperature range of interest. The results may be plotted as specific volume versus temperature as shown in FIG. 5, which illustrates a representative example of a dilatometric study of branched poly(vinyl acetate). Since the elbow in volume-temperature studies is not sharp (measurements of $T_g$ using dilatometric studies show a dispersion of about 20-30° C.), the two straight lines below and above the transition are extrapolated until they meet. The extrapolated meeting point is taken as the $T_g$. A representative example of an apparatus that can be used to measure a $T_g$ via dilatometric studies is the Dilatometer DIL 402 PC (available from Netzsch, Inc., Exton, Pa.).

Thermal methods can also be used to measure the $T_g$ of a bulk sample. Two closely related methods are differential thermal analysis (DTA), and differential scanning calorimetry (DSC). Both methods yield peaks relating to endothermic and exothermic transitions and show changes in heat capacity. A representative example of a DTA apparatus is the Rheometrics STA 1500 which provides simultaneous thermal analysis via DTA and DSC.

In addition to the information that can be produced by a DTA, the DSC method also yields quantitative information relating to the enthalpic changes in the polymer (the heat of fusion of the temperature, $\Delta H_f$). The DSC method uses a servo system to supply energy at a varying rate to the sample and the reference, so that the temperatures of the two stay equal. The DSC output plots energy supplied against average temperature. By this method, the areas under the peaks can be directly related to the enthalpic changes quantitatively.

Referring to FIG. 3, the $T_g$ can be taken as the temperature at which one-half of the increase in the heat capacity, $\Delta C_p$, has occurred. The increase in $\Delta C_p$ is associated with the increased molecular motion of the polymer.

A method of separating a transient phenomenon such as a hysteresis peak from the reproducible result of the change in heat capacity is obtained via the use of modulated DSC. Here, a sine wave is imposed on the temperature ramp. A real-time computer analysis allows a plot of not only the whole data but also its transient and reproducible components. Representative examples of modulated DSC apparatuses are those in the Q Series™ DSC product line from TA Instruments, New Castle, Del.

Another representative example of an apparatus that uses DSC as the base technology for measuring the $T_g$ is a micro thermal analyzer, such as the μTA™ 2990 product from TA Instruments. A micro thermal analyzer can have an atomic force microscope (AFM) that is used in conjunction with a thermal analyzer. The instrument can be used to analyze individual sample domains identified from the AFM images. In a micro thermal analyzer such as the μTA™ 2990, the AFM measurement head can contain an ultra-miniature probe that functions as a programmable heat source and temperature sensor. A micro thermal analyzer, therefore, can provide information similar to that from traditional thermal analysis, but on a microscopic scale. For example, the μTA™ 2990 can provide images of a sample in terms of its topography, relative thermal conductivity and relative thermal diffusivity. The μTA™ 2990 can also provide spatial resolution of about 1 μm with a thermal probe and atomic resolution with regular AFM probes. Other advantages of the μTA™ 2990 is that it can heat the polymer sample from ambient to about 500° C. at heating rates up to 1500° C./minute which allows for rapid thermal characterization (e.g., in less than 60 seconds), and it can hold the sample isothermically over a broad range of temperatures (e.g., −70 to 300° C.), which allows for thermal characterization over a broad temperature range.

Since the notion of the glass-rubber transition stems from a softening behavior, mechanical methods can provide very direct determination of the $T_g$ for a bulk sample. Two fundamental types of measurement prevail: the static or quasi-static methods, and the dynamic methods. For amorphous polymers and many types of semicrystalline polymers in which the crystallinity does not approach 100%, stress relaxation, Gehman, and/or Glash-Berg instrumentation provide, through static measurement methods, rapid and inexpensive scans of the temperature behavior of new polymers before going on to more complex methods. Additionally, there are instruments that can be employed to measure dynamic mechanical spectroscopy (DMS) or dynamic mechanical analysis (DMA) behavior. A representative example of an apparatus for a DMA method is the DMA 242, available from Netzsch, Inc., Exton, Pa.

Another method for studying the mechanical spectra of all types of polymers, especially those that are not self-supporting, is torsional braid analysis (TBA). In this case the polymer is dipped onto a glass braid, which supports the sample. The braid is set into a torsional motion. The sinusoidal decay of the twisting action is recorded as a function of time as the temperature is changed. Because the braid acts as a support medium, the absolute magnitudes of the transitions are not obtained; only their temperatures and relative intensities are recorded.

The $T_g$ of a bulk sample of a polymer can also be observed by utilizing electromagnetic methods. Representative examples of electromagnetic methods for the characterization of transitions in polymers are dielectric loss (e.g., using the DEA 2970 dielectric analyzer, available from TA Instruments, New Castle, Del.) and broad-line nuclear magnetic resonance (NMR).

If the thickness of the coating polymer is ultra thin (i.e., less than 1 micron), it may be useful to utilize specialized measuring techniques, at least to compare the results with the values determined by measuring a bulk polymer sample to ensure that the bulk values are not affected by the thickness of the polymer layer. Specialized techniques may be useful because it has recently been observed that the $T_g$ of a polymer can be influenced by the thickness of the polymer layer. Researchers, for example, have observed that polystyrene films on hydrogen-passivated Si had glass transition temperatures that were lower than the bulk value if the thickness of the films was less than 0.04 microns. See Forest et al., Effect of Free Surfaces on the $T_g$ of Thin Polymer Films, Physical Review Letters 77(10), 2002-05 (September 1996).

Brillouin light scattering (BLS) can be used to measure the $T_g$ of a polymer in an ultra thin film. The ultra thin films can be prepared by spin casting the polymer onto a substrate (e.g., the same substrate used to support the coating polymer on the stent). A spinning apparatus is available, for example, from Headway Research, Inc., Garland, Tex. BLS can also be used to find the $T_g$ of a polymer in a bulk sample. In BLS studies of bulk polymers, one measures the velocity $v_L$ of the bulk longitudinal phonon, where $v_L = (C_{11}/\rho)^{1/2}$, $C_{11}$ is the longitudinal elastic constant, and $\rho$ is the density. Since $C_{11}$ is a strong function of $\rho$, as the sample temperature is changed, the temperature dependence of $v_L$ exhibits an abrupt change in slope at the temperature at which the thermal expansivity is discontinuous, i.e., the $T_g$. For thin films, BLS probes the elastic properties through observation of film-guided acoustic phonons. The guided acoustic modes are referred to as Lamb modes for freely standing films. For further discussion of the application of BLS for measuring $T_g$, see Forest et al., Effect of Free Surfaces on the Glass Transition Temperature of Thin Polymer Films, Physical Review Letters 77(10), 2002-05 (September 1996) and Forest et al. Mater. Res. Soc. Symp. Proc. 407, 131 (1996).

The $T_g$ of an ultra thin polymer film can also be determined by using three complementary techniques: local thermal analysis, ellipsometry and X-ray reflectivity. See, e.g., Fryer et al., Dependence of the Glass Transition Temperature of Polymer Films on Interfacial Energy and Thickness, Macromolecules 34, 5627-34 (2001). Using ellipsometry (e.g., with a Rudolph Auto EL nulling ellipsometer) and X-ray reflectivity (e.g., with a Scintag XDS 2000), the $T_g$ is determined by measuring changes in the thermal expansion of the film. Using local thermal analysis, on the other hand, the $T_g$ is determined by measuring changes in the heat capacity and thermal conductivity of the film and the area of contact between a probe and the polymer surface.

Table 1 lists the $T_g$ for some of the polymers used in the embodiments of the present invention. The cited temperature is the temperature as reported in the noted reference and is provided by way of illustration only and is not meant to be limiting.

TABLE 1

| POLYMER | $T_g$ (°K) | METHOD USED TO CALCULATE $T_g$ | REFERENCE |
| --- | --- | --- | --- |
| EVAL | 330 | DMA | Tokoh et al., Chem. Express, 2(9), 575-78 (1987) |
| Poly(n-butyl methacrylate) | 293 | Dilatometry | Rogers et al., J. Phys. Chem., 61, 985-90 (1957) |

TABLE 1-continued

| POLYMER | $T_g$ (°K) | METHOD USED TO CALCULATE $T_g$ | REFERENCE |
| --- | --- | --- | --- |
| Poly(ethylene-co-vinyl acetate) | 263 | DSC and DMA | Scott et al., J. Polym. Sci., Part A, Polym. Chem., 32(3), 539-55 (1994) |
| Poly(ethylene terephthalate) | 343.69 | DSC | Sun et al., J. Polym. Sci., Part A, Polym. Chem., 34(9), 1783-92 (1996) |
| Poly(vinylidene fluoride) | 243 | Dielectric relaxation | Barid et al., J. Mater. Sci., 10(7), 1248-51 (1975) |
| Poly(p-phenylene sulfide) | 361 | DSC | Ding, et al., Macromolecules, 29(13), 4811-12 (1996) |
| Poly(6-aminocaproic acid) | 325 | DSC | Gee et al., Polymer, 11, 192-97 (1970) |
| Poly(methyl methacrylate) | 367 | DSC | Fernandez-Martin, et al., J. Polym. Sci., Polym. Phys. Ed., 19(9), 1353-63 (1981) |
| Poly(vinyl alcohol) | 363 | Dilatometry | Fujii et al., J. Polym. Sci., Part A, 2, 2327-47 (1964) |
| Poly(epsilon-caprolactone) | 208 | DSC | Loefgren et al., Macromolecules, 27(20), 5556-62 (1994) |

As noted above, "polymer" as used herein is inclusive of homopolymers, copolymers, terpolymers etc., including random, alternating, block, cross-linked, blends and graft variations thereof. By using the methods of measurement described above, one may observe more than one $T_g$ for some of these types of polymers. For example, some polymer blends that exhibit two phase systems can have more than one $T_g$. Additionally, some semicrystalline polymers can have two glass transitions, especially when they have a higher percent crystallinity. See Edith A. Turi, Thermal Characterization of Polymeric Materials, Academic Press, Orlando, Fla. (1981). Bulk-crystallized polyethylene and polypropylene, for example, can have two glass transition temperatures at a relatively high percent crystallinity. The lower of the two transitions is represented as $T_g(L)$, which can be the same as the conventional $T_g$ at zero crystallinity. The higher transition is designated as $T_g(U)$ and becomes more detectable as the crystallinity increases. The difference, $\Delta T_g = T_g(U) - T_g(L)$, tends to approach zero as the fractional crystallinity $\chi$ approaches zero.

It has also been reported that block and graft copolymers can have two separate glass transition temperatures. For some of these polymers, each $T_g$ can be close to the $T_g$ of the parent homopolymer. The following Table 2 lists the glass transition temperatures for representative examples of block and graft copolymers. As illustrated by Table 2, most of these block and graft copolymers exhibit two glass transition temperatures. The cited temperatures were reported in Black and Worsfold, J. Appl. Polym. Sci., 18, 2307 (1974) who used a thermal expansion technique to measure the temperatures, and are provided by way of illustration only.

TABLE 2

| $M_1$ | $M_2$ | % $M_1$ | Total MW | Lower $T_g$ (°K) | Upper $T_g$ (°K) |
| --- | --- | --- | --- | --- | --- |
| α-Methylstyrene | Vinyl acetate | 18 | 103,000 | 308 | 455 |
| α-Methylstyrene | Vinyl chloride | 67 | 39,000 | 265 | 455 |
| α-Methylstyrene | Styrene | 45 | 61,000 | 400 | — |
| Styrene | Methyl methacrylate | 40 | 70,000 | — | 371 |

TABLE 2-continued

| $M_1$ | $M_2$ | % $M_1$ | Total MW | Lower $T_g$ (°K) | Upper $T_g$ (°K) |
|---|---|---|---|---|---|
| Styrene | Butyl acrylate | 46 | 104,000 | 218 | 372 |
| Styrene | Ethylene oxide | 50 | 40,000 | 201 | 373 |
| Styrene | Isoprene | 50 | 1,000,000 | 198 | 374 |
| Styrene | Isobutylene | 40 | 141,000 | 204 | 375 |
| Methyl Methacrylate | Ethyl acrylate | 56 | 162,000 | 250 | 388 |
| Methyl Methacrylate | Vinyl acetate | 50 | 96,000 | 311 | 371 |
| Methyl Methacrylate | Ethyl methacrylate | 50 | 104,000 | 342 | 379 |

In one embodiment of the present invention, if the polymer exhibits more than one $T_g$, the polymer is exposed to a temperature equal to or greater than the lowest observed $T_g$. It is believed that by exposing a polymer to a temperature equal to or greater than the lowest $T_g$, the release rate of the polymer should be reduced to a measurable extent because at least some of the amorphous domains will be modified during the process. In another embodiment, if the polymer exhibits more than one $T_g$, the polymer is exposed to a temperature equal to or greater than the highest observed $T_g$. By exposing the polymer to the highest $T_g$, it is believed that one can maximize the release rate reduction.

As noted above, in one embodiment, the drug polymeric drug coating can be exposed to a temperature equal to or greater than the $T_g$ and less than the $T_m$ of the polymer. There are several types of methods that can be used to measure the $T_m$ of a polymer. For example, the melting temperature can be observed by measuring visual, physical, and thermal properties as a function of temperature.

$T_m$ can be measured by visual observation by using microscopic techniques. For instance, the disappearance of crystallinity in a semicrystalline or crystalline polymer can be observed with a microscope, with the sample housed between crossed nicols (i.e., an optical material that functions as a prism, separating light rays that pass through it into two portions, one of which is reflected away and the other transmitted). As a polymer sample is heated, the sharp X-ray pattern characteristic of crystalline material gives way to amorphous halos at the $T_m$.

Another way of observing the $T_m$ is to observe the changes in specific volume with temperature. Since melting constitutes a first-order phase change, a discontinuity in the volume is expected. The $T_m$ should give a discontinuity in the volume, with a concomitant sharp melting point. Because of the very small size of the crystallites in bulk crystallized polymers, however, most polymers melt over a range of several degrees. The $T_m$ is the temperature at which the last trace of crystallinity disappears. This is the temperature at which the largest and/or most "perfect" crystals are melting.

Alternatively, the $T_m$ can be determined by using thermomechanical analysis (TMA) that uses a thermal probe (e.g., available from Perkin Elmer, Norwalk, Conn.). The $T_m$ can also be determined with a thermal-based method. For example, a differential scanning calorimetry (DSC) study can be used to determine the $T_m$. The same process for DSC as described above for the determination of $T_g$ can be used to determine the $T_m$. Referring to FIG. 3, the $T_m$ of the representative polymer is the peak of curve 64.

Table 3 lists the $T_g$ for some of the polymers used in the embodiments of the present invention. The cited temperature is the temperature as reported in the noted reference and is provided by way of illustration only and is not meant to be limiting.

TABLE 3

| POLYMER | $T_m$ (°K) | METHOD USED TO CALCULATE $T_m$ | REFERENCE |
|---|---|---|---|
| EVAL | 437.3 | DMA | Tokoh et al., Chem. Express, 2(9), 575-78 (1987) |
| Poly(ethylene terephthalate) | 526.38 | DSC | Sun et al., J. Polym. Sci., Part A, Polym. Chem., 34(9), 1783-92 (1996) |
| Poly(vinylidene fluoride) | 444 | Dielectric relaxation | Barid et al., J. Mater. Sci., 10(7), 1248-51 (1975) |
| Poly(p-phenylene sulfide) | 560 | DSC | Ding, et al., Macromolecules, 29(13), 4811-12 (1996) |
| Poly(6-aminocaproic acid) | 498 | DSC | Gee et al., Polymer, 11, 192-97 (1970) |
| Poly(vinyl alcohol) | 513 | TMA | Fujii et al., J. Polym. Sci., Part A, 2, 2327-47 (1964) |
| Poly(epsilon-caprolactone) | 330.5 | DSC | Loefgren et al., Macromolecules, 27(20), 5556-62 (1994) |

In the embodiments of the present invention, the thermal treatment process can be used to reduced the release rate of an active agent from polymeric coatings having various coating structures. Referring to FIG. 1A, for instance, reservoir layer 24 has a polymer and an active agent. The polymer in reservoir layer 24 can be exposed to a temperature sufficient to reduce the release rate of the active agent from reservoir layer 24. In one embodiment, the polymer in reservoir layer 24 is exposed to a temperature equal to or greater than the $T_g$ of the polymer. In another embodiment, the polymer in reservoir layer 24 is exposed to a temperature equal to or greater than the $T_g$ and less than the $T_m$ of the polymer. In other embodiments, the polymer is exposed to (1) the $T_c$ of the polymer; (2) the annealing temperature of the polymer or (3) a temperature equal to 0.9 times the $T_m$ of the polymer.

The thermal treatment process can also be directed to a coating having a barrier layer as illustrated in FIG. 1B. Referring to FIG. 1B, an active agent can be deposited in cavities 26, and covered by barrier layer 30. In one embodiment of the present invention, the polymer in barrier layer 30 is exposed to a temperature equal to or greater than the $T_g$ of the polymer. In other embodiments, the polymer in barrier layer 30 is exposed to (1) a temperature equal to or greater than the $T_g$ and less than the $T_m$ of the polymer; (2) the $T_c$ of the polymer; (3) the annealing temperature of the polymer or (4) a temperature equal to 0.9 times the $T_m$ of the polymer.

The thermal treatment process can also be directed to a polymeric coating having a polymeric reservoir layer 24 covered at least in part by barrier layer 30 as illustrated by FIGS. 1C and 1D. Referring to FIG. 1D, reservoir layer 24 can be deposited on optional primer layer 32 and covered by barrier layer 30. In one embodiment, the polymers in reservoir layer 24 and barrier layer 30, respectively, are simultaneously exposed to a temperature equal to or greater than the $T_g$ of the polymers in the two layers. In other embodiments, the polymers in reservoir layer 24 and barrier layer 30 are simultaneously exposed to (1) a temperature equal to or greater than the $T_g$ and less than the $T_m$ of the polymers; (2) the $T_c$ of the polymers; (3) the annealing temperature of the polymers or (4) a temperature equal to 0.9 times the $T_m$ of the polymers.

The polymers in reservoir layer 24 and barrier layer 30 can be simultaneously exposed to the appropriate temperature if, for instance, the polymer in reservoir layer 24 has the same or substantially the same thermal properties as the polymer in barrier layer 30. For example, the polymer in reservoir layer 24 can have about the same $T_c$ or $T_g$ as the polymer in barrier layer 30. The polymers in reservoir layer 24 and barrier layer 30 can also be simultaneously exposed to the appropriate temperature if the temperature used to conduct the thermal treatment is sufficiently high to surpass the selected temperature (e.g., annealing temperature, $T_c$, etc.) for each polymer.

The thermal treatment process can also be conducted to selectively treat the various polymeric layers. For example, one can selectively treat the polymeric layers by constructing a coating that has layers with polymers having different thermal properties. The coatings illustrated by FIGS. 1C and 1D, for instance, can be constructed so that the polymer in reservoir layer 24 has different thermal properties than the polymer in barrier layer 30.

In one embodiment, if the polymer in reservoir layer 24 has a $T_c$ that is higher than the $T_c$ of the polymer in barrier layer 30, the polymeric coating is exposed to a temperature greater than the $T_c$ of the polymer in barrier layer 30, but less than the $T_c$ of the polymer in reservoir layer 24. This process can also be used if the annealing temperature or $T_g$ of the polymer in reservoir layer 24 is greater than the annealing temperature or $T_g$ of the polymer in barrier layer 30.

In another embodiment, if the polymer in reservoir layer 24 has a $T_c$ that is lower than the $T_c$ of the polymer in barrier layer 30, the polymeric coating is exposed to a temperature greater than the $T_c$ of the polymer in reservoir layer 34, but less than the $T_c$ of the polymer in barrier layer 30. This process can also be used if the annealing temperature or $T_g$ of the polymer in reservoir layer 24 is lower than the annealing temperature or $T_g$ of the polymer in barrier layer 30.

In yet another embodiment, the heat source can be directed to only certain portions of the stent or only for certain durations so that the diffusion rates of the active agent from the polymer differs in various portions of the coating. Referring to FIG. 1E, for example, the polymeric material in barrier layer 30B can be exposed to a thermal treatment, whereas the polymeric material in barrier layer 30A is not. As a result, the release rate of the active agent from the polymeric material in barrier 30B can be lower than the release rate of the active agent from the polymeric material in barrier 30A. The release rate difference can result because, for example, the polymer of barrier layer 30B will have a higher percent crystallinity than the polymeric material in barrier layer 30A.

In another example, the implantable device can have two or more segments along the longitudinal axis of the implantable device, such as a first segment, a second segment and a third segment. The radiation could be directed substantially only at the first segment and the third segment, for instance, by using a cauterizer tip. Alternatively, the radiation could be set higher for the first and third segments, or the radiation could be directed at the first and third segments for a longer duration than the second segment. As a result, the polymer along the first segment and the third segment would have a greater percent crystallinity than the polymer along the second segment. Therefore, the diffusion rates of the active agent from the polymer matrix along the first segment and the third segment would be less than the diffusion rate along the second segment. In one embodiment, the first and third segments can be on the opposing end portions of the stent, the second segment being the middle region of the stent.

The exposure temperature should not adversely affect the characteristics of the active agent present in the coating. In order to prevent possible degradation of the active agent or the polymer in the coating, additives can be mixed with the polymer before or during the coating process to shift the thermal profile of the polymer (i.e., decrease the $T_g$ and $T_m$ of the polymer). For example, a plasticizer, which is usually a low molecular weight nonvolatile molecule, can be dissolved with the polymer before the application process. The plasticizer can be an active agent. A representative example of an additive is dioctyl phthalate.

The selected duration of the thermal treatment can depend on the selected exposure temperature, the thermal characteristics of the polymer in the coating, the thermal stability of the active agent and the desired release rate, among other factors. The duration of the thermal treatment, for instance, can be from about 30 seconds to about 7 hours. By way of example, in a thermal treatment of a coating having EVAL and actinomycin D, the polymer can be exposed to a temperature of about 473° K for about 2 minutes, or about 353° K. for about 2 hours.

In another embodiment, if the polymer in the coating is semicrystalline, the time that the coating is exposed to radiation can be limited so that the percent crystallinity is not maximized throughout the entire thickness of the coating. In other words, the shallower regions of the coating will have a higher percent crystallinity than the deeper regions. The degree of crystallinity decreases as a function of the depth of the coating. In a particular example, if the coating is defined as having four regions, with the fourth region as the deepest, by controlling the thermal treatment, the first or shallowest region would have a higher percent crystallinity, followed by the second, third and lastly fourth region, which would have the lowest degree of crystallinity. One of ordinary skill in the art will understand that the duration and temperature of the exposure will depend on the desired diffusion rate of the active agent through the polymer, and the inherent characteristics of the polymers used in the coating.

Sterilization of the Implantable Device

After the implantable device has been coated according to the various embodiments of the present invention, the implantable device can be sterilized by various methods. In an embodiment of the present invention, the particular procedure used to sterilize the coating can also be used conduct the thermal treating process. For example, an electron beam or a gas sterilization procedure can be used to conduct the thermal treating process and to sterilize the coating that has been formed on the stent. Representative examples of gas sterilization procedures include those using ethylene oxide, steam/ autoclaving, hydrogen peroxide and peracetic acid. The sterilization processes can be modified so that the temperature produced during the process is sufficient to decrease the release rate of the active agent from the polymeric coating, but does not significantly degrade the active agent. For example, for the electron beam sterilization procedure, the exposure temperature is at least a function of dose, dose rate, heat capacity of the coating material and the degree of insulation of the product. These variables can be adjusted so that the coating is exposed to the appropriate temperature.

Forming an Active Agent-Containing Coating

The composition containing the active agent can be prepared by first forming a polymer solution by adding a predetermined amount of a polymer to a predetermined amount of a compatible solvent. "Solvent" is defined as a liquid substance or composition that is compatible with the components of the composition and is capable of dissolving the component(s) at the concentration desired in the composition.

The polymer can be added to the solvent at ambient pressure and under anhydrous atmosphere. If necessary, gentle heating and stirring and/or mixing can be employed to effect dissolution of the polymer into the solvent, for example 12 hours in a water bath at about 60° C.

Sufficient amounts of the active agent can then be dispersed in the blended composition of the polymer and the solvent. The active agent can be mixed with the polymer solution so that the active agent forms a true solution or becomes saturated in the blended composition. If the active agent is not completely soluble in the composition, operations including mixing, stirring, and/or agitation can be employed to effect homogeneity of the residues. The active agent can also be first added to a solvent that is capable of more readily dissolving the active agent prior to admixing with the polymer composition. The active agent can also be added so that the dispersion is in fine particles.

The polymer can comprise from about 0.1% to about 35%, more narrowly from about 0.5% to about 20% by weight of the total weight of the composition, the solvent can comprise from about 59.9% to about 99.8%, more narrowly from about 79% to about 99% by weight of the total weight of the composition, and the active agent can comprise from about 0.1% to about 40%, more narrowly from about 1% to about 9% by weight of the total weight of the composition. Selection of a specific weight ratio of the polymer and solvent is dependent on factors such as, but not limited to, the material from which the device is made, the geometrical structure of the device, the type and amount of the active agent employed, and the release rate desired.

Representative examples of polymers that can be combined with the active agent for the reservoir layer include EVAL; poly(butyl methacrylate); copolymers of vinyl monomers with each other and olefins, such as ethylene-methyl methacrylate copolymers, acrylonitrile-styrene copolymers, ABS resins, and ethylene-vinyl acetate copolymers; poly(hydroxyvalerate); poly(L-lactic acid); poly(epsilon-caprolactone); poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; polyamides, such as Nylon 66 and polycaprolactam; alkyd resins; polycarbonates; polyoxymethylenes; polyimides; polyethers; epoxy resins; polyurethanes; rayon; rayon-triacetate; cellulose acetate; cellulose butyrate; cellulose acetate butyrate; cellophane; cellulose nitrate; cellulose propionate; cellulose ethers; and carboxymethyl cellulose.

EVAL is functionally a very suitable choice of polymer. EVAL copolymer refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. Ethylene vinyl alcohol copolymers are available commercially from companies such as Aldrich Chemical Company, Milwaukee, Wisc., or EVAL Company of America, Lisle, Ill., or can be prepared by conventional polymerization procedures that are well known to one of ordinary skill in the art.

The copolymer of EVAL allows for good control capabilities of the release rate of the active agent. As a general rule, an increase in the amount of the ethylene comonomer content decreases the rate that the active agent is released from the copolymer matrix. The release rate of the active agent typically decreases as the hydrophilicity of the copolymer decreases. An increase in the amount of the ethylene comonomer content increases the overall hydrophobicity of the copolymer, especially as the content of vinyl alcohol is concomitantly reduced. It is also thought that the release rate and the cumulative amount of the active agent that is released is directly proportional to the total initial content of the agent in the copolymer matrix. Accordingly, a wide spectrum of release rates can be achieved by modifying the ethylene comonomer content and the initial amount of the active agent.

Poly(butylmethacrylate) ("PBMA") and ethylene-vinyl acetate copolymers can also be especially suitable polymers for the reservoir layer. In one embodiment, the polymer in the reservoir coating is a mixture of PBMA and an ethylene-vinyl acetate copolymer.

Representative examples of solvents include chloroform, acetone, water (buffered saline), dimethylsulfoxide (DMSO), propylene glycol methyl ether (PM), iso-propylalcohol (IPA), n-propylalcohol, methanol, ethanol, tetrahydrofuran (THF), dimethylformamide (DMF), dimethylacetamide (DMAC), benzene, toluene, xylene, hexane, cyclohexane, pentane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof.

The active agent may be any substance capable of exerting a therapeutic or prophylactic effect in the practice of the present invention. Examples of such active agents include antiproliferative, antineoplastic, antiinflammatory, antiplatelet, anticoagulant, antifibrin, antithrombin, antimitotic, antibiotic, and antioxidant substances as well as combinations thereof. An example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of antineoplastics include paclitaxel and docetaxel. Examples of antiplatelets, anticoagulants, antifibrins, and antithrombins include aspirin, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocor). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck & Co., Whitehouse Station, N.J.), calcium channel blockers (such as Nifedipine), colchicine, fibroblast growth factor (FGF) antagonists, histamine antagonist, LOVASTATIN (an inhibitor of HMG-CoA reductase, a cholesterol lowering drug from Merck & Co.), monoclonal antibodies (such as PDGF receptors), nitroprusside, phosphodiesterase inhibitors, prostaglandin inhibitor (available form Glazo), Seramin (a PDGF antagonist), serotonin blockers, thioprotease inhibitors, triazolopyrimidine (a PDGF antagonist), and nitric oxide. Other therapeutic substances or agents that may be appropriate include alpha-interferon, genetically engineered epithelial cells, dexamethasone, estradiol, clobetasol propionate, cisplatin, insulin sensitizers, receptor tyrosine kinase inhibitors and carboplatin. Exposure of the composition to the active agent should not adversely alter the active agent's composition or characteristic. Accordingly, the particular active agent is selected for compatibility with the blended composition.

Rapamycin can be a very suitable choice of active agent. Additionally, 40-O-(2-hydroxy)ethyl-rapamycin, or a functional analog or structural derivative thereof, can be an especially functional choice of active agent. The chemical structure for 40-O-(2-hydroxy)ethyl-rapamycin is as follows:

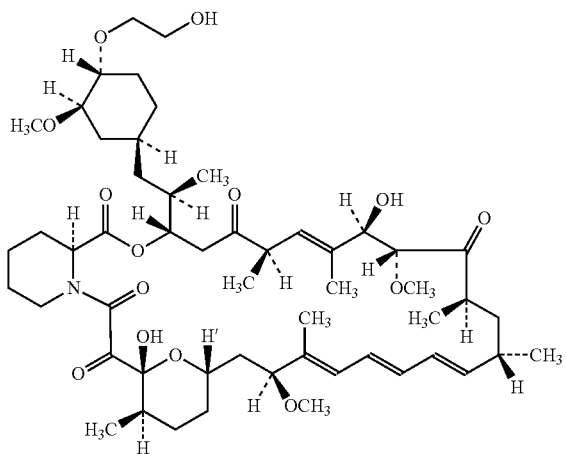

Examples of analogs or derivatives of 40-O-(2-hydroxy) ethyl-rapamycin include but are not limited to 40-O-(3-hydroxy)propyl-rapamycin and 40-O-[2-(2-hydroxy)ethoxy] ethyl-rapamycin.

40-O-(2-hydroxy)ethyl-rapamycin binds to the cytosolic immunophyllin FKBP12 and inhibits growth factor-driven cell proliferation, including that of T-cells and vascular smooth muscle cells. The actions of 40-O-(2-hydroxy)ethyl-rapamycin occur late in the cell cycle (i.e., late G1 stage) compared to other immunosuppressive agents such as tacrolimus or cyclosporine which block transcriptional activation of early T-cell-specific genes. Since 40-O-(2-hydroxy)ethyl-rapamycin can act as a potent anti-proliferative agent, it is believed that 40-O-(2-hydroxy)ethyl-rapamycin can be an effective agent to treat restenosis by being delivered to a local treatment site from a polymeric coated implantable device such as a stent.

The release rate of 40-O-(2-hydroxy)ethyl-rapamycin can be advantageously controlled by various methods and coatings as described herein. In particular, by using the methods and coatings of the present invention, the release rate of the 40-O-(2-hydroxy)ethyl-rapamycin, or analog or derivative thereof, can be less than about 50% in 24 hours.

When the 40-O-(2-hydroxy)ethyl-rapamycin is blended with a polymer for the reservoir layer, the ratio of 40-O-(2-hydroxy)ethyl-rapamycin, or analog or derivative thereof, to polymer by weight in the reservoir layer can be about 1:2.8 to about 1:1. The 40-O-(2-hydroxy)ethyl-rapamycin, or analog or derivative thereof, in the reservoir layer can be in the amount of about 50 μg to about 500 μg, more narrowly about 90 μg to about 350 μg, and the polymer is in the amount of about 50 μg to about 1000 μg, more narrowly about 90 μg to about 500 μs.

The dosage or concentration of the active agent required to produce a therapeutic effect should be less than the level at which the active agent produces unwanted toxic effects and greater than the level at which non-therapeutic effects are obtained. The dosage or concentration of the active agent required to inhibit the desired cellular activity of the vascular region, for example, can depend upon factors such as the particular circumstances of the patient; the nature of the trauma; the nature of the therapy desired; the time over which the ingredient administered resides at the vascular site; and if other bioactive substances are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Forming a Barrier Layer to Reduce the Rate of Release

In some coatings, the release rate of the active agent may be too high to be clinically useful. For example, as shown in Example 22 below, for 40-O-(2-hydroxy)ethyl-rapamycin the percentage of 40-O-(2-hydroxy)ethyl-rapamycin released from a stent coating without a barrier layer in 24 hours was determined to be 58.55% as measured in a porcine serum release rate procedure. The release rate from the coating of Example 22 may be too high for a treatment using 40-O-(2-hydroxy)ethyl-rapamycin as the active agent. A barrier layer can reduce the rate of release or delay the time at which the active agent is released from the reservoir layer.

In accordance with one embodiment, the barrier layer can be applied on a selected region of the reservoir layer to form a rate reducing member. The barrier layer can be applied to the reservoir layer prior to or subsequent to the heat treatment. The composition for the barrier layer can be substantially free of active agents. Alternatively, for maximum blood compatibility, compounds such as polyethylene glycol, heparin, heparin derivatives having hydrophobic counterions, or polyethylene oxide can be added to the barrier layer, or disposed on top of the barrier layer.

The choice of polymer for the barrier layer can be the same as the selected polymer for the reservoir. The use of the same polymer, as described for some of the embodiments, significantly reduces or eliminates any interfacial incompatibilities, such as lack of adhesion, which may exist in the employment of two different polymeric layers.

Polymers that can be used for a barrier layer include the examples of polymers listed above for the reservoir layer. Representative examples of polymers for the barrier layer also include polytetrafluoroethylene, perfluoro elastomers, ethylene-tetrafluoroethylene copolymer, fluoroethylene-alkyl vinyl ether copolymer, polyhexafluoropropylene, low density linear polyethylenes having high molecular weights, ethylene-olefin copolymers, atactic polypropylene, polyisobutene, polybutylenes, polybutenes, styrene-ethylene-styrene block copolymers, styrene-butylene-styrene block copolymers, styrene-butadiene-styrene block copolymers, and ethylene methacrylic acid copolymers of low methacrylic acid content.

EVAL is functionally a very suitable choice of polymer for the barrier layer. The copolymer can comprise a mole percent of ethylene of from about 27% to about 48%. Fluoropolymers are also a suitable choice for the barrier layer composition. For example, polyvinylidene fluoride (otherwise known as KYNAR, available from ATOFINA Chemicals, Philadelphia, Pa.) can be dissolved in acetone, methylethylketone, dimethylacetamide, and cyclohexanone, and can optionally be combined with EVAL to form the barrier layer composition. Also, solution processing of fluoropolymers is possible, particularly the low crystallinity varieties such as CYTOP available from Asahi Glass and TEFLON AF available from DuPont. Solutions of up to about 15% (wt/wt) are possible in perfluoro solvents, such as FC-75 (available from 3M under the brand name FLUORINERT), which are non-polar, low boiling solvents. Such volatility allows the solvent to be easily and quickly evaporated following the application of the polymer-solvent solution to the implantable device.

Poly(butylmethacrylate) ("PBMA") and ethylene-vinyl acetate copolymers can also be especially suitable polymers for the barrier layer. In one embodiment, poly(butylmethacrylate) ("PBMA") can be used for the barrier layer. PBMA, for example, can be dissolved in a solution of xylene, acetone and HFE FLUX REMOVER (Techspray, Amarillo, Tex.). In another embodiment, the polymer in the barrier layer is a mixture of PBMA and an ethylene-vinyl acetate copolymer.

The barrier layer can also be styrene-ethylene/butylene-styrene block copolymer. Styrene-ethylene/butylene-styrene block copolymer, e.g., Kraton G-series, can be dissolved in non-polar solvents such as, but not limited to, toluene, xylene, and decalin.

Other choices of polymers for the rate-limiting membrane include, but are not limited to, ethylene-anhydride copolymers; and ethylene-acrylic acid copolymers having, for example, a mole % of acrylic acid of from about 2% to about 25%. The ethylene-anhydride copolymer available from Bynel adheres well to EVAL and thus would function well as a barrier layer over a reservoir layer made from EVAL. The copolymer can be dissolved in organic solvents, such as dimethylsulfoxide and dimethylacetamide. Ethylene vinyl acetate polymers can be dissolved in organic solvents, such as toluene and n-butyl acetate. Ethylene-acrylic acid copolymers can be dissolved in organic solvents, such as methanol, isopropyl alcohol, and dimethylsulfoxide.

Yet another choice of polymer for the rate-limiting membrane is a cross-linked silicone elastomer. Loose silicone and silicone with very low cross-linking are thought to cause an inflammatory biological response. However, it is believed that a thoroughly cross-linked silicone elastomer, having low levels of leachable silicone polymer and oligomer, is an essentially non-inflammatory substance. Silicone elastomers, such as Nusil MED-4750, MED-4755, or MED2-6640, having high tensile strengths, for example between 1200 psi and 1500 psi, will likely have the best durability during crimping, delivery, and expansion of a stent as well as good adhesion to a reservoir layer, e.g., EVAL or the surface of an implantable device.

The composition for a rate-reducing membrane or diffusion barrier layer can be prepared by the methods used to prepare a polymer solution as described above. The polymer can comprise from about 0.1% to about 35%, more narrowly from about 1% to about 20% by weight of the total weight of the composition, and the solvent can comprise from about 65% to about 99.9%, more narrowly from about 80% to about 98% by weight of the total weight of the composition. Selection of a specific weight ratio of the polymer and solvent is dependent on factors such as, but not limited to, the type of polymer and solvent employed, the type of underlying reservoir layer, and the method of application.

Forming a Primer Layer

The presence of an active agent in a polymeric matrix can interfere with the ability of the matrix to adhere effectively to the surface of the device. Increasing the quantity of the active agent reduces the effectiveness of the adhesion. High drug loadings in the coating can hinder the retention of the coating on the surface of the device. A primer layer can serve as a functionally useful intermediary layer between the surface of the device and an active agent-containing or reservoir coating. The primer layer provides an adhesive tie between the reservoir coating and the device—which, in effect, would also allow for the quantity of the active agent in the reservoir coating to be increased without compromising the ability of the reservoir coating to be effectively contained on the device during delivery and, if applicable, expansion of the device.

Representative examples of suitable polymers for the primer layer include, but are not limited to, polyisocyanates, such as triisocyanurate and polyisocyanate; polyether; polyurethanes based on diphenylmethane diisocyanate; acrylates, such as copolymers of ethyl acrylate and methacrylic acid; titanates, such as tetra-iso-propyl titanate and tetra-n-butyl titanate; zirconates, such as n-propyl zirconate and n-butyl zirconate; silane coupling agents, such as 3-aminopropyltriethoxysilane and (3-glydidoxypropyl)methyldiethoxysilane; high amine content polymers, such as polyethyleneamine, polyallylamine, and polylysine; polymers with a high content of hydrogen bonding groups, such as polyethylene-co-polyvinyl alcohol, ethylene vinyl acetate, and melamine formaldehydes; and unsaturated polymers and prepolymers, such as polycaprolactone diacrylates, polyacrylates with at least two acrylate groups, and polyacrylated polyurethanes. With the use of unsaturated prepolymers, a free radical or UV initiator can be added to the composition for the thermal or UV curing or cross-linking process, as is understood by one of ordinary skill in the art.

Representative examples of polymers that can be used for the primer material also include those polymers that can be used for the reservoir layer as described above. The use of the same polymer can significantly reduce or eliminate interfacial incompatibilities, such as lack of an adhesive tie or bond, which may exist with the employment of two different polymeric layers.

EVAL is a very suitable choice of polymer for the primer layer. The copolymer possesses good adhesive qualities to the surface of a stent, particularly stainless steel surfaces, and has illustrated the ability to expand with a stent without any significant detachment of the copolymer from the surface of the stent.

By way of example, and not limitation, the polymer can comprise from about 0.1% to about 35%, more narrowly from about 1% to about 20% by weight of the total weight of the composition, and the solvent can comprise from about 65% to about 99.9%, more narrowly from about 80% to about 98% by weight of the total weight of the primer composition. A specific weight ratio is dependent on factors such as the material from which the implantable device is made, the geometrical structure of the device, the choice of polymer-solvent combination, and the method of application.

With the use of the thermoplastic polymers for the primer, such as EVAL, polycaprolactone, poly(lactide-co-glycolide), poly(hydroxybutyrate), etc., the deposited primer composition can be exposed to a heat treatment at a temperature range greater than about the $T_g$ and less than about the $T_m$ of the selected polymer. This treatment is conducted to the actual composition of the polymer and solvent. The heat treatment can be terminated when the coating becomes or extended for a period of time subsequent to the drying of the primer coating. Alternatively, the treatment can be conducted subsequent to the evaporation of the solvent, when the polymer is in a dry form. Unexpected results have been discovered with treatment of the composition under this temperature range, specifically strong adhesion or bonding of the coating to the metallic surface of a stent. The device should be exposed to the heat treatment for any suitable duration of time that would allow for the formation of the primer coating on the surface of the device.

Table 4 lists the $T_g$ and $T_m$ for some of the polymers that can be used for the optional primer layer. The cited exemplary temperature and time for exposure are provided by way of illustration and are not meant to be limiting.

TABLE 4

| Polymer | $T_g$ (°K) | $T_m$ (°K) | Exemplary Temperature (°K) | Exemplary Duration of Time For Heating |
|---|---|---|---|---|
| EVAL | 330 | 437.3 | 413 | 4 hours |
| polycaprolactone | 208 | 330.5 | 323 | 2 hours |
| ethylene vinyl acetate (e.g., 33% vinyl acetate content) | 309 | 336 | 318 | 2 hours |
| Polyvinyl alcohol | 363 | 513 | 438 | 2 hours |

If the polymer of the primer layer is a combination or blend of polymers, then the selected temperature is determined as previously described. For example, if the primer is a blend of EVAL and polyvinyl alcohol, the $T_g$ of the blend can be calculated by using a DSC method.

Forming a Finishing Layer

Depending on the polymer used for the reservoir or barrier layers, it may be advantageous to form a finishing layer that is especially biocompatible on the surface of the coating that is exposed to the biological lumen when inserted into a patient. The finishing layer can be formed on the surface of the coating subsequent to the thermal treatment. Representative examples of biocompatible polymers or biocompatible agents for the finishing layer include, but are not limited to EVAL, polyethylene oxide, polyethylene glycol, hyaluronic acid, polyvinyl pyrrolidone, heparin, heparin derivatives such as those having hydrophobic counterions, and phosphylcholine.

Methods For Applying the Compositions to the Device

The optional primer composition can first be applied to the stent. Application of the composition can be by any conventional method, such as by spraying the composition onto the prosthesis or by immersing the prosthesis in the composition. Operations such as wiping, centrifugation, blowing, or other web-clearing acts can also be performed to achieve a more uniform coating. Briefly, wiping refers to physical removal of excess coating from the surface of the stent; centrifugation refers to rapid rotation of the stent about an axis of rotation; and blowing refers to application of air at a selected pressure to the deposited coating. Any excess coating can also be vacuumed off the surface of the device.

After the application of the primer composition, the solvent in the composition on the stent should be removed before the application of the reservoir layer composition. The solvent can be allowed to evaporate or evaporation can be induced by heating the device at a predetermined temperature for a predetermined period of time. For example, the device can be heated at a temperature of about 60° C. for about 10 minutes to about 24 hours. The heating can be conducted in an anhydrous atmosphere and at ambient pressure and should not exceed the temperature which would adversely affect the active agent. The heating can also be conducted under a vacuum condition.

The composition containing the active agent can be applied to a designated region of the primer coating or the surface of the device. As noted above for the primer layer, the solvent can be removed from the composition by allowing the solvent to evaporate or heating the stent.

The diffusion barrier layer can be formed on a designated region of the active agent-containing coating subsequent to the evaporation of the solvent and the drying of the polymer for the active agent-containing coating. Alternatively, in embodiments in which a polymeric reservoir coating is not employed, the rate-reducing membrane may be formed directly over active-agent containing cavities within the surface of the prosthesis. The above-described processes can be similarly repeated for the formation of the diffusion barrier layer.

Depending on the coating process, residual water and oxygen may remain in the coating after the baking processes used to remove the solvents. For example, after a coating process that occurs in a 60% relative humidity coating environment, a coating with EVAL can have about 2% residual content of water (w/w). These residual components may adversely react with the polymer during the thermal treatment process if they are not removed before hand. The stents can advantageously be processed to remove essentially all of the water and/or free oxygen that may have been absorbed by the composition during the coating process. The stents, for example, can be placed in a dessicator and then heated in a convection oven to remove any residual water. The stents can also be placed in a vacuum oven or in a gas chamber before undergoing the thermal treatment process. If a gas chamber is used, the chamber can be in communication with a gas source that provides an inert gas such as nitrogen or argon that can remove the water and free oxygen in the coating. The duration required for the process to remove residual water can be determined by a Karl Fisher, or TGA study.

Examples of the Device

Examples of implantable devices for the present invention include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (EL-GILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

The embodiments of the present invention may be particularly useful for the coatings of small vessel stents. Small vessels stents can be generally categorized as having inner diameters of less than 2.5 mm in an expanded state. Because of their small size, small vessel stents offer unique challenges for drug delivery. In particular, as compared to conventionally sized stents, small vessel stents have a greater surface:volume ratio. Therefore, when a small vessel stent is inserted into a biological lumen, the vessel tissue surrounding a small vessel stent is exposed to a greater concentration of polymer. The present invention can be used to reduce the amount of polymer that is needed on the stent structure while maintaining an efficacious release rate. The present invention, therefore, can reduce the risk of an inflammatory response by the vessel tissue when small stents are used as a drug delivery device in small vessels.

Method of Use

In accordance with the above-described method, the active agent can be applied to a device, e.g., a stent, retained on the device during delivery and released at a desired control rate and for a predetermined duration of time at the site of implantation. A stent having the above-described coating layers is useful for a variety of medical procedures, including, by way of example, treatment of obstructions caused by tumors in bile ducts, esophagus, trachea/bronchi and other biological passageways. A stent having the above-described coating layers is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously, or by surgery, into the femoral artery, brachial artery, femoral vein, or brachial vein, and advanced into the appropriate blood vessel by steering the catheter through the vascular system under fluoroscopic guidance. A stent having the above-described coating layers may then be expanded at the desired area of treatment. A post insertion angiogram may also be utilized to confirm appropriate positioning.

EXAMPLES

The embodiments of the present invention will be illustrated by the following set forth examples.

Example 1

35 13 mm PENTA stents (available from Guidant Corporation) were coated by spraying a 2% (w/w) solution of poly (ethylene-co-vinyl alcohol) (44 mole % ethylene) ("EVAL") in 98% (w/w) dimethylacetamide. The solvent was removed by baking at 140° C. for 2 hours. A solution of 1.9% (w/w) EVAL and 0.7% (w/w) 40-O-(2-hydroxy)ethyl-rapamycin in a mixture of 68.2% (w/w) dimethylacetamide and 29.2% (w/w) ethanol was spray coated onto the stents to a thickness with a target of 175 µg of 40-O-(2-hydroxy)ethyl-rapamycin on each stent. The stents were then baked at 50° C. for 2 hours. A barrier layer was formed by spraying the stents with a 4% (w/w) solution of EVAL in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 µg of polymer, and a measured average dry weight of 43±3 µg of polymer. For the reservoir layer, the target drug:polymer ratio was 1:2.857, the target dry weight for the entire reservoir coating was 675 µg and the average actual dry weight was 683±19 µg. Also for the reservoir layer, the average total drug content of the stent coatings was determined by the process described in Example 2. The average drug content was 133 µg or 152 µg/cm$^2$. For the barrier layer, the target dry weight of polymer was 300 µg and the measured average dry weight was 320±13 µg.

Example 2

A drug-coated stent was placed in a volumetric flask. An appropriate amount of the extraction solvent acetonitrile with 0.02% BHT as protectant was added (e.g., in a 10 ml volumetric flask, with about 9 ml solvent added). The flask was sonicated for a sufficient time to extract all of the drug from the reservoir region. Then, the solution in the flask was filled to mark with the solvent solution. The drug solution was the analyzed by HPLC. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 µM particle size), maintained at a temperature of 40° C. The mobile phase consisted of 75% acetonitrile and 25% 20 mMolar ammonium acetate. The flow rate was set on 1 ml/min. The HPLC release rate results were quantified by comparing the results with a reference standard. The total drug content of the stent was then calculated.

Example 3

34 13 mm PENTA stents were coated by spraying a 2% (w/w) solution of EVAL and 98% (w/w) dimethylacetamide. The solvent was removed by baking at 140° C. for 2 hours. A solution of 1.9% (w/w) EVAL and 1.1% (w/w) 40-O-(2-hydroxy)ethyl-rapamycin in a mixture of 67.9% (w/w) dimethylacetamide and 29.1% (w/w) ethanol was spray coated onto the stents to a thickness with a target of 275 µg of 40-O-(2-hydroxy)ethyl-rapamycin on each stent. The stents were then baked at 50° C. for 2 hours. A barrier layer was formed by spraying the stents with a 4% (w/w) solution of EVAL in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 μg of polymer, and a measured average dry weight of 43±3 μg of polymer. For the reservoir layer, the target drug:polymer ratio was 1:1.75, the target dry weight for the entire reservoir coating was 757 μg and the average actual dry weight was 752±23 μg. Also for the reservoir layer, the average total drug content of the stent coatings was determined by the process described in Example 2. The average drug content was 205 μg or 235 μg/cm². For the barrier layer, the target dry weight of polymer was 200 μg and the measured average dry weight was 186±13 μg.

Example 4

24 13 mm PENTA stents were coated by spraying a 2% (w/w) solution of EVAL and 98% (w/w) dimethylacetamide. The solvent was removed by baking at 140° C. for 2 hours. A solution of 1.9% (w/w) EVAL and 1.2% (w/w) 40-O-(2-hydroxy)ethyl-rapamycin in a mixture of 67.8% (w/w) dimethylacetamide and 29.1% (w/w) ethanol was spray coated onto the stents to a thickness with a target of 325 μg of 40-O-(2-hydroxy)ethyl-rapamycin on each stent. The stents were then baked at 50° C. for 2 hours. A barrier layer was formed by spraying the stents with a 4% (w/w) solution of EVAL in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 μg of polymer, and a measured average dry weight of 41±2 μg of polymer. For the reservoir layer, the target drug:polymer ratio was 1:1.6, the target dry weight for the entire reservoir coating was 845 μg and the average actual dry weight was 861±16 μg. Also for the reservoir layer, the average total drug content of the stent coatings was determined by the process described in Example 2. The average drug content was 282 μg or 323 μg/cm². For the barrier layer, the target dry weight of polymer was 125 μg and the measured average dry weight was 131±9 μg.

Example 5

This Example 5 is referred to as the "Release Rate Profile Procedure." A drug-coated stent was placed on a stent holder of a Vankel Bio-Dis release rate tester (Vankel, Inc., Cary, N.C.). The stent was dipped into an artificial medium which stabilizes the 40-O-(2-hydroxy)ethyl-rapamycin in the testing solution, including a phosphate buffer saline solution (10 mM, pH 7.4) with 1% TRITON X-100 (Sigma Corporation), for a designated amount of time (e.g., 3 hours). Then the solution was analyzed for the amount of drug released from the stent coating using an HPLC process. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 μm particle size), maintained at a temperature of 40° C. The mobile phase consisted of 75% acetonitrile and 25% 20 mMolar ammonium acetate. The flow rate was set on 1 ml/min. After the drug solution was analyzed by HPLC the results were quantified by comparing the release rate results with a reference standard.

If the experimental protocol required that the stent coating be subjected to experimental conditions for an additional time, the stent was then dipped in a fresh medium solution for the necessary amount of time (e.g., another 3 hours) and the drug released in the solution was analyzed again according to the HPLC procedure described above. The procedure was repeated according to the number of data points required. The release rate profile could then be generated by plotting cumulative drug released in the medium vs. time.

Example 6

The release rate of 40-O-(2-hydroxy)ethyl-rapamycin from the stents with coatings produced by the processes under Examples 1, 3 and 4 were tested using the in vitro HPLC process as described in Example 5. The solution for each stent underwent two HPLC runs, and the results were averaged.

The following Table 5 summarizes the results of the release rate procedure for two stents from Example 1:

TABLE 5

| | Time (hrs) | | | | | | |
|---|---|---|---|---|---|---|---|
| | 3 | 6 | 9 | 12 | 23 | 32 | 48 |
| Cumulative Release from Stent 1 (μg) | 3.72 | 5.62 | 7.12 | 8.43 | 12.28 | 15.31 | 20.28 |
| Cumulative Release from Stent 2 (μg) | 4.18 | 6.53 | 8.54 | 10.29 | 15.64 | 19.66 | 26.3 |

The following Table 6 summarizes the results of the release rate procedure for two stents from Example 3:

TABLE 6

| | Time (hrs) | | | | | | |
|---|---|---|---|---|---|---|---|
| | 3 | 6 | 9 | 12 | 23 | 32 | 48 |
| Cumulative Release from Stent 1 (μg) | 29.73 | 45.35 | 57.79 | 68.19 | 95.2 | 110.85 | 130.75 |
| Cumulative Release from Stent 2 (μg) | 26.36 | 41.2 | 53.5 | 63.99 | 93.93 | 112.31 | 135.7 |

The following Table 7 summarizes the results of the release rate procedure for two stents from Example 4:

TABLE 7

| | Time (hrs) | | | | | | |
|---|---|---|---|---|---|---|---|
| | 3 | 6 | 9 | 12 | 23 | 32 | 48 |
| Cumulative Release from Stent 1 (μg) | 46.24 | 67.4 | 82.79 | 94.92 | 124.72 | 141.96 | 165.12 |
| Cumulative Release from Stent 2 (μg) | 44.66 | 66.74 | 82.26 | 94.49 | 123.92 | 140.07 | 159.65 |

Figure 6:
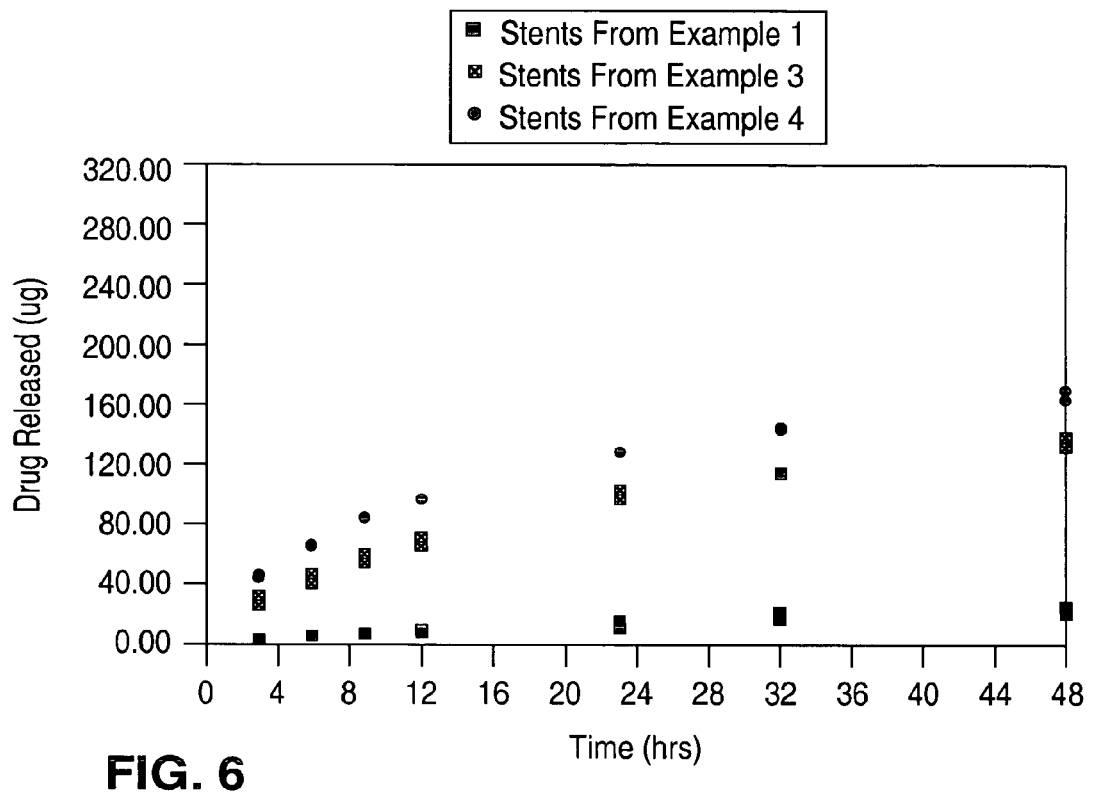
FIG. 6 is a graph showing the release rate of an active agent from stent coatings as referred to in Example 6.

A comparison of the release rates for the stents from Examples 1, 3 and 4 is graphically shown in FIG. 6.

Example 7

The following Example 7 is referred to as the "3 day In Vivo Release Rate Procedure" or the "9 day In Vivo Release Rate Procedure," depending on the number of days the stents are inserted into the experimental animal. The following are the materials used for this Example:

1. Experimental animal: One 30-45 kg Yorkshire cross pig;
2. BMW™ wires 0.014", 190 cm;
3. Guide wire 0.035", 190 cm;
4. Viking guide catheters, 7 F;
5. Introducer sheaths (8-10 F);
6. ACS 20/20 Indeflator™ Inflation Device;
7. Saline; solution with heparin;
8. Nitroglycerin, Lidocaine, other inotropic/chronotropic drugs;
9. Standard surgical equipment, anesthetic, and medications as necessary;
10. Respiratory and hemodynamic monitoring systems;
11. Positive pressure ventilator and associated breathing circuits;
12. ACT machine and accessories;
13. PTCA accessories;
14. Ambulatory defibrillator;
15. Fluoroscopy equipment; and
16. Non-ionic contrast agent.

The following was the procedure used for this Example:

A. Animal Preparation.
1. Administer Aspirin (325 mg PO) once daily starting one day prior to stent implantation.
2. Sedate the pig.
3. Intubate the trachea via an oral approach.
4. Deliver isoflurane (up to about 5%) to achieve and maintain an adequate plane of anesthesia.
5. Shave the sheath introduction area free of hair and scrub the surgical site with surgical soap and/or antiseptic solution.
6. Place a 7 F introducer sheath into the right or left femoral artery.
7. Obtain an arterial blood sample for a baseline ACT.
8. Administer heparin 200 units/kg IV (not to exceed 100,000 units) and obtain a blood sample for measurement of ACT 5-10 minutes later.
9. Repeat heparin as needed to maintain ACT ≧300 seconds.
10. Measure and record arterial blood pressure, heart rate and electrocardiogram (ECG).

B. Angiography for Vessel Selection.
1. Advance the guiding catheter over the guidewire into the aortic arch and cannulate the desired vessel.
2. Administer nitroglycerin (200 µg) intra-luminally prior to baseline angiography.
3. Perform baseline angiogram and record images on cine.
4. With the diameter of the guiding catheter as a reference, select vasculature that will allow a target stent to artery ratio of about 1.1:1.0.

C. Stent Preparation and Deployment.
1. Perform online QCA and measure baseline proximal, target, and distal reference sites.
2. Administer nitroglycerin (200 µg) intra-luminally prior to stent deployment, then as needed to control coronary artery vasospasm.
3. Inspect the stent delivery system. Ensure that the stent is correctly positioned on the balloon. Inspect the stent for any abnormalities.
4. Flush guidewire lumen with heparinized saline until fluid exits the guidewire notch.
5. Prepare Indeflator/syringe with diluted (approximately 50:50) contrast medium.
6. Attach syringe to test catheter inflation port; use standard techniques to fill the inflation lumen with diluted contrast.
7. Purge syringe and test catheter inflation lumen of all air.
8. Purge Indeflator of all air and attach to test catheter inflation port.
9. Position an appropriate guidewire in the distal bed of the target artery.
10. Insert the stent delivery system through the guiding catheter over the guidewire.
11. Advance the stent delivery system to the pre-selected arterial deployment site.
12. Position balloon for inflation.
13. Refer to IFU for inflation strategy. If no IFU available, inflate the balloon at a slow steady rate to a pressure that expands the stent to the desired diameter. Hold at this pressure for 30 seconds.
14. Record inflated balloon by pulling image on cine. Perform on-line QCA and measure the inflated balloon diameter.
15. Deflate balloon by pulling negative pressure. While withdrawing the system, observe tactually and fluoroscopically. Record any resistance.
16. Administer nitroglycerin (200 µg) intra-luminally.
17. Assess patency, deployment, and placement of stent via coronary angiography.
18. Assess TIMI angiographic low grade.
19. Record on cine and video.
20. Measure post-proximal, target, and distal MLD with QCA.
21. Repeat Section C with remaining stent delivery system.
22. Measure and record heart rate, arterial blood pressure and electrocardiogram (ECG).

D. Stent Procedure End.
1. Remove the guidewire, guiding catheter and introducer sheath.
2. Remove introducer sheath from the femoral artery.
3. Apply pressure to the femoral artery at the side of sheath entry.
4. Allow the animal to recover from anesthesia in an individual cage.
5. Give Buprenorphine (0.05 mg/kg) PRN as needed for pain.
6. Administer Ticlopidine (250 mg PO) and aspirin (325 mg PO) once daily until date of follow-up angiography.

E. Study End.
1. Euthanize the p microbolometer ig with an overdose of barbiturates and/or potassium chloride.
2. Excise the heart without flushing the vessels.
3. Harvest all stented arteries.
4. Remove the stent from all treated arteries and place them in dark colored amber vials for subsequent drug concentration analysis.
5. Snap freeze the arterial tissue in liquid nitrogen and store at −70° C. until subsequent analysis of tissue for drug concentrations as determined by HPLC.

The stents harvested from the experimental animals were tested using an HPLC procedure to determine how much drug remained on the stents. A drug-coated stent removed from the experimental animal was placed in a volumetric flask. An appropriate amount of the extraction solvent acetonitrile with 0.02% BHT as protectant was added (e.g., in a 10 ml volumetric flask, with about 9 ml solvent added). The flask was sonicated for a sufficient time to extract all of the drug from the reservoir region. Then, the solution in the flask was filled to mark with the solvent solution. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 μm particle size), maintained at a temperature of 40° C. The mobile phase consisted of 75% acetonitrile and 25% 20 mMolar ammonium acetate. The flow rate was set on 1 ml/min The HPLC release rate results were quantified by comparing the results with a reference standard. The total drug released in vivo was the difference between the average drug loaded on the stents and the amount of drug remaining on the stents after the stent implantation into the experimental animal.

Example 8

The release rate of 40-O-(2-hydroxy)ethyl-rapamycin from the stents with coatings produced by the process under Example 1 were tested using a 3 day in vivo process as described in Example 7. In particular, stents from Example 1 were implanted into experimental animals and then the stents were tested by HPLC to determine how much 40-O-(2-hydroxy)ethyl-rapamycin diffused from the stent coating into the blood vessel. According to the HPLC analysis, 21.8 μg of the 40-O-(2-hydroxy)ethyl-rapamycin was released from the coating in 3 days, or 16.4% of the total drug content of the coating.

Example 9

The release rate of 40-O-(2-hydroxy)ethyl-rapamycin from the stents with coatings produced by the process under Example 3 were tested using a 3 day in vivo process as described in Example 7. In particular, stents from Example 3 were implanted into experimental animals and then the stents were tested by HPLC to determine how much 40-O-(2-hydroxy)ethyl-rapamycin diffused from the stent coating into the blood vessel. According to the HPLC analysis, 7.8 μg of the 40-O-(2-hydroxy)ethyl-rapamycin was released from the coating in 3 days, or 3.8% of the total drug content of the coating.

Example 10

The release rate of 40-O-(2-hydroxy)ethyl-rapamycin from the stents with coatings produced by the process under Example 4 were tested using a 3 day in vivo process as described in Example 7. In particular, stents from Example 4 were implanted into experimental animals and then the stents were tested by HPLC to determine how much 40-O-(2-hydroxy)ethyl-rapamycin diffused from the stent coating into the blood vessel. According to the HPLC analysis, 50.8 μg of the 40-O-(2-hydroxy)ethyl-rapamycin was released from the coating in 3 days, or 18% of the total drug content of the coating.

Example 11

The release rate of 40-O-(2-hydroxy)ethyl-rapamycin from the stents with coatings produced by the process under Example 3 were tested using a 9 day in vivo process as described in Example 7. In particular, stents from Example 3 were implanted into experimental animals and then the stents were tested by HPLC to determine how much 40-O-(2-hydroxy)ethyl-rapamycin diffused from the stent coating into the blood vessel. According to the HPLC analysis, 29.7% of the 40-O-(2-hydroxy)ethyl-rapamycin was released from the coating in 9 days.

Example 12

The release rate of 40-O-(2-hydroxy)ethyl-rapamycin from the stents with coatings produced by the process under Example 4 were tested using a 9 day in vivo process as described in Example 7. In particular, stents from Example 4 were implanted into experimental animals and then the stents were tested by HPLC to determine how much 40-O-(2-hydroxy)ethyl-rapamycin diffused from the stent coating into the blood vessel. According to the HPLC analysis, 39.4% of the 40-O-(2-hydroxy)ethyl-rapamycin was released from the coating in 9 days.

Example 13

A 13 mm PIXEL stent (available from Guidant Corporation) was coated. The stent had a yellowish-gold coating that included ethylene vinyl alcohol copolymer and actinomycin D. The ends of the stent were heated with a cauterizer tip for fifteen (15) seconds at a current setting of 2.2 Amps, which corresponded to a temperature of about 106° C. at a distance of about 0.006 inches from the stent.

After the stent was exposed to heat from the cauterizer tip, the stent was submerged in a 50% (w/w) methanol:water bath. After twenty-four (24) hours, the stent was observed to have drug present at the stent end rings as indicated by a yellowish hue. The middle section of the stent, however, was clear, indicating that the drug had been released through the polymer. This process was repeated on 40 stents yielding similar results for all the stents.

Example 14

13 mm PIXEL stents were coated. The stents had yellowish-gold coatings that included ethylene vinyl alcohol copolymer and actinomycin D. The stents were separated into three experimental groups, and the ends of the stents were heated with a cauterizer tip according to the parameters shown in Table 8 for each group. After the stents were exposed to heat from the cauterizer tip, the stent was submerged in a 50% (w/w) methanol:water bath. After twenty-four (24) hours, the stents were observed as summarized in Table 8.

TABLE 8

| Experimental Group | Current (Amps) | Exposure Time (Seconds) | Observation |
| --- | --- | --- | --- |
| 1 | 2.0 | 10 | Least gold coloration in the end sections compared to the stents from Experimental Groups 2 and 3, indicating the least amount of drug remaining in the stent coating. |
| 2 | 2.2 | 8 | Moderate gold coloration in the end sections. |
| 3 | 2.4 | 5 | Most gold coloration in the end sections compared to the stents from Experimental Groups 1 and 2 indicating the most amount of drug remaining in the stent coating. |

It was observed that the coating in the middle section of the stents, which did not have significant exposure to heat from the cauterizer tip, was clear. This indicates that the drug had been eluted from the stents. On the other hand, the end rings of the stents which had been exposed to heat from the cauterizer tip still appeared gold in color, indicating the presence of drug in the stent coating. The results above indicate that varying the amount of time and heat exposure can modify the elution rate of drug from the stent.

Example 15

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 26 μg of polymer, and a measured average dry weight of 28±3 μg of polymer. For the reservoir layer, the target drug:polymer ratio was 1:1.25, and the measured average drug content was 128 μg. For the barrier layer, the measured average dry weight was 84 μg.

Example 16

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 26 μg of polymer, and a measured average dry weight of 28±2 μg of polymer. For the reservoir layer, the target drug:polymer ratio was 1:1.5, and the measured average drug content was 130 μg. For the barrier layer, the measured average dry weight was 81 μg.

After the solvent had been substantially removed and the coatings had been formed, a select number of stents were then heat treated by exposing the stents to a heat of 80° C. for 2 hours.

Example 17

The release rate of 40-O-(2-hydroxy)ethyl-rapamycin from the stents with coatings produced by the processes under Examples 15 and 16 were tested using the process described in Example 5. The following Table 9 summarizes the results of the release rate procedure for three stents from Example 15:

TABLE 9

| | Time (hrs) | | | | | | |
|---|---|---|---|---|---|---|---|
| | 3 | 6 | 9 | 12 | 24 | 32 | 48 |
| Cumulative Release from Stent 1 (μg) | 15.44 | 24.63 | 32.20 | 38.43 | 56.04 | 64.81 | 77.36 |
| Cumulative Release from Stent 2 (μg) | 12.70 | 21.29 | 28.57 | 34.55 | 51.19 | 59.27 | 71.15 |
| Cumulative Release from Stent 3 (μg) | 13.00 | 21.92 | 29.31 | 35.40 | 52.55 | 60.48 | 72.05 |

The following Table 10 summarizes the results of the release rate procedure for three stents from Example 16:

TABLE 10

| | Time (hrs) | | | | | | |
|---|---|---|---|---|---|---|---|
| | 3 | 6 | 9 | 12 | 24 | 32 | 48 |
| Cumulative Release from Stent 1 (μg) | 5.52 | 9.37 | 12.73 | 15.71 | 24.33 | 29.20 | 38.02 |
| Cumulative Release from Stent 2 (μg) | 6.73 | 10.86 | 14.39 | 17.41 | 25.99 | 30.29 | 38.00 |
| Cumulative Release from Stent 3 (μg) | 5.76 | 9.14 | 12.02 | 14.50 | 21.21 | 24.61 | 31.23 |

Figure 7:
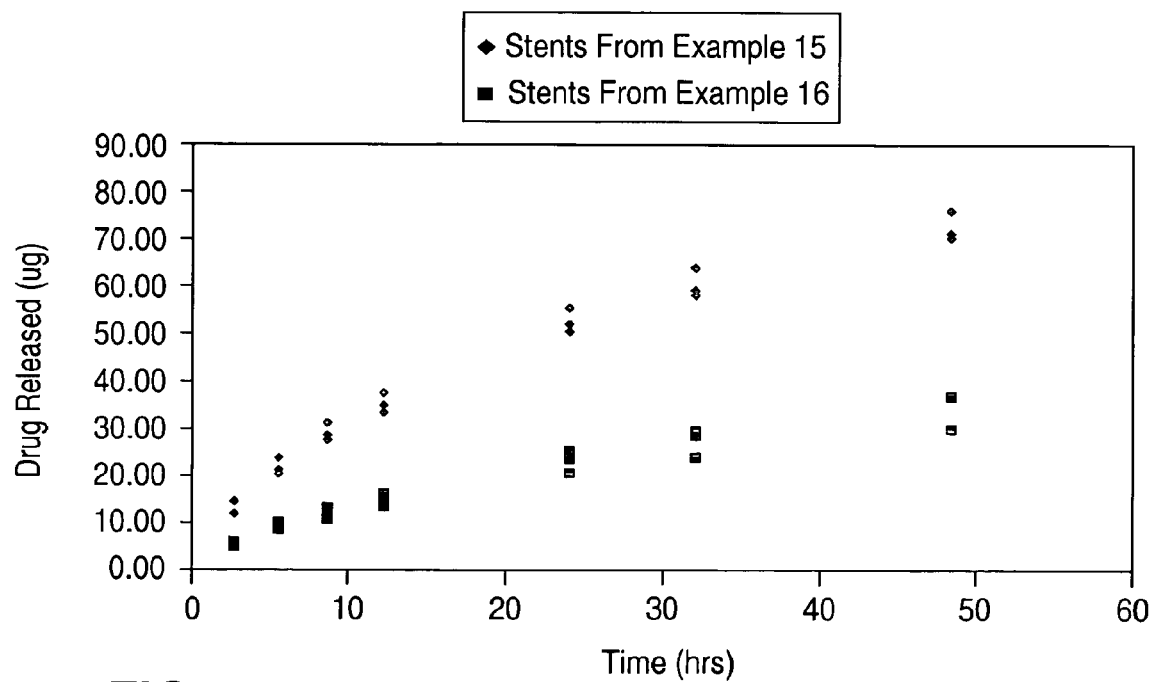
FIG. 7 is a graph showing the release rate of an active agent from stent coatings as referred to in Example 17.

A comparison of the release rates for the stents from Examples 15-16 is graphically shown in FIG. 7. The results unexpectedly show that the stent coatings that were exposed to thermal treatment in Example 16 have a significantly lower release rate than the stent coatings of Example 15.

Example 18

This Example 18 is referred to as the "Porcine Serum Release Rate Procedure." A drug-coated stent was placed on a stent holder of a Vankel Bio-Dis release rate tester. The stent was dipped into porcine serum, with 0.1% sodium azide added, for 24 hrs. The stent was removed from the porcine serum and the drug solution analyzed by an HPLC procedure to determine how much drug was released into the porcine serum. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 μm particle size), maintained at a temperature of 40° C. The mobile phase consisted of 75% acetonitrile and 25% 20 mMolar ammonium acetate. The flow rate was set on 1 ml/min. The HPLC release rate results were quantified by comparing the results with a reference standard.

Example 19

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w)

ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 45±1 μg of polymer. For the reservoir layer, the drug:polymer ratio was 1:1, and the measured average drug content was 151 μg as determined by Example 2. For the barrier layer, the measured average dry weight was 234 μg.

After the coatings were formed on the stents, a select number of stents were tested for the drug release rate from the coatings according to the procedure described in Example 18. It was determined that the average drug released in 24 hours was 32.6 μg, or 21.6% of the total.

Example 20

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 44±3 μg of polymer. For the reservoir layer, the drug:polymer ratio was 1:1.8, and the measured average drug content was 97 μg as determined by Example 2. For the barrier layer, the measured average dry weight was 184 μg.

After the coatings were formed on the stents, a select number of stents were tested for the drug release rate from the coatings according to the procedure described in Example 18. It was determined that the average drug released in 24 hours was 24.1 μg, or 24.8% of the total.

Example 21

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 41±1 μg of polymer. For the reservoir layer, the drug:polymer ratio was 1:1.8, and the measured average drug content was 227 μg as determined by Example 2. For the barrier layer, the measured average dry weight was 181 μg.

After the coatings were formed on the stents, a select number of stents were tested for the drug release rate from the coatings according to the procedure described in Example 18. It was determined that the average drug released in 24 hours was 27.5 μg, or 12.1% of the total.

Example 22

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. No barrier layer was applied for this Example.

A select number of stents were analyzed to quantify the coating components. For the primer layer, there was a target dry weight of 40 μg of polymer, and a measured average dry weight of 44±2 μg of polymer. For the reservoir layer, the drug:polymer ratio was 1:1.8, and the measured average drug content was 221 μg as determined by Example 2.

After the coatings were formed on the stents, a select number of stents were tested for the drug release rate from the coatings according to the procedure described in Example 18. It was determined that the average drug released in 24 hours was 129.4 μg, or 58.55% of the total.

Example 23

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 42 μg of polymer. For the reservoir layer, the drug:polymer ratio was 1:1.5, and the measured average drug content was 184 μg as determined by Example 2. For the barrier layer, the measured average dry weight was 81 μg.

After the coatings were formed on the stents, a select number of stents were tested for the drug release rate from the coatings according to the procedure described in Example 18. It was determined that the average drug released in 24 hours was 70.1 μg, or 38.1% of the total.

Example 24

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 µg of polymer, and a measured average dry weight of 45±1 µg of polymer. For the reservoir layer, the drug:polymer ratio was 1:1.75, and the measured average drug content was 200 µg as determined by Example 2. For the barrier layer, the measured average dry weight was 180 µg.

After the coatings were formed on the stents, a select number of stents were tested for the drug release rate from the coatings according to the procedure described in Example 18. It was determined that the average drug released in 24 hours was 39.0 µg, or 19.5% of the total.

Example 25

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 µg of polymer, and a measured average dry weight of 41±4 µg of polymer. For the reservoir layer, the drug:polymer ratio was 1:1, and the measured average drug content was 167 µg as determined by Example 2. For the barrier layer, the measured average dry weight was 184 µg.

After the coatings were formed on the stents, a select number of stents were tested for the drug release rate from the coatings according to the procedure described in Example 18. It was determined that the average drug released in 24 hours was 6.0 µg, or 3.6% of the total.

Example 26

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 26 µg of polymer, and a measured average dry weight of 24±2 µg of polymer. For the reservoir layer, the drug:polymer ratio was 1:1.25, and the measured average drug content was 120 µg as determined by Example 2. For the barrier layer, the measured average dry weight was 138 µg.

After the coatings were formed on the stents, a select number of stents were tested for the drug release rate from the coatings according to the procedure described in Example 18. It was determined that the average drug released in 24 hours was 11.0 µg, or 9.2% of the total.

Example 27

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) polybutyl-methacrylate ("PBMA"), 5.7% (w/w) acetone, 50% (w/w) xylene and 43.3% (w/w) HFE FLUX REMOVER (Techspray, Amarillo, Tex.). Another 2 hour bake at 50° C. was performed to remove the solvent.

A select number of stents were analyzed to quantify the coating components. For the primer layer, there was a target dry weight of 40 µg of polymer, and a measured average dry weight of 44±4 µg of polymer. For the reservoir layer, the drug:polymer ratio was 1:1, and the measured average drug content was 183 µg as determined by Example 2. For the barrier layer, the measured average dry weight was 168 µg.

After the coatings were formed on the stents, a select number of stents were tested for the drug release rate from the coatings according to the procedure described in Example 18. It was determined that the average drug released in 24 hours was 21.6 µg, or 11.8% of the total.

Example 28

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) PBMA, 5.7% (w/w) acetone, 50% (w/w) xylene and 43.3% (w/w) HFE FLUX REMOVER. Another 2 hour bake at 50° C. was performed to remove the solvent.

A select number of stents were analyzed to quantify the coating components. For the primer layer, there was a target dry weight of 40 µg of polymer, and a measured average dry weight of 41±2 µg of polymer. For the reservoir layer, the drug:polymer ratio was 1:1.8, and the measured average drug content was 102 µg as determined by Example 2. For the barrier layer, the measured average dry weight was 97 µg.

After the coatings were formed on the stents, a select number of stents were tested for the drug release rate from the coatings according to the procedure described in Example 18. It was determined that the average drug released in 24 hours was 9.1 µg, or 8.9% of the total.

Example 29

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) PBMA, 5.7% (w/w) acetone, 50% (w/w) xylene and 43.3% (w/w) HFE FLUX REMOVER (Techspray, Amarillo, Tex.). Another 2 hour bake at 50° C. was performed to remove the solvent.

A select number of stents were analyzed to quantify the coating components. For the primer layer, there was a target dry weight of 26 µg of polymer, and a measured average dry weight of 27±2 µg of polymer. For the reservoir layer, the drug:polymer ratio was 1:1.25, and the measured average drug content was 120 μg as determined by Example 2. For the barrier layer, the measured average dry weight was 68 μg.

After the coatings were formed on the stents, a select number of stents were tested for the drug release rate from the coatings according to the procedure described in Example 18. It was determined that the average drug released in 24 hours was 22.0 μg, or 18.3% of the total.

Example 30

A select number of stents from Example 3 were tested for the drug release rate from the coatings according to the procedure described in Example 18. It was determined that the average drug released in 24 hours was 22.8 μg, or 11.1% of the total.

Example 31

A select number of stents from Example 4 were tested for the drug release rate from the coatings according to the procedure described in Example 18. It was determined that the average drug released in 24 hours was 57.0 μg, or 20.2% of the total.

Example 32

Two stents were coated by spraying a 2% (w/w) solution of EVAL and 98% (w/w) dimethylacetamide to form a primer layer. For the primer layer, there was a target dry weight of 100 μg of polymer, and the measured dry weights were 93 μg and 119 μg, respectively. The two stents were then coated with an EVAL-40-O-(2-hydroxy)ethyl-rapamycin blend at a drug:polymer ratio of 2:1 to produce a reservoir layer. After application, it was determined that the reservoir layers had weights of 610 μg and 590 μg, respectively. From the total weight of the reservoir layers and the drug:polymer ratio, it was estimated that the coatings contained about 407 μg and 393 μg of 40-O-(2-hydroxy)ethyl-rapamycin, respectively. Polymeric barrier layers were also applied to the stents and it was determined that the weights of the barrier layers were 279 μg and 377 μg, respectfully.

The stents from this Example were then sterilized using an ethylene oxide sterilization process. In particular, the stents were placed in a chamber and exposed to ethylene oxide gas for 6 hours at 130-140° F., with a relative humidity of 45-80%. The stents were then aerated for about 72 hours at 110-130° F.

Figure 8:
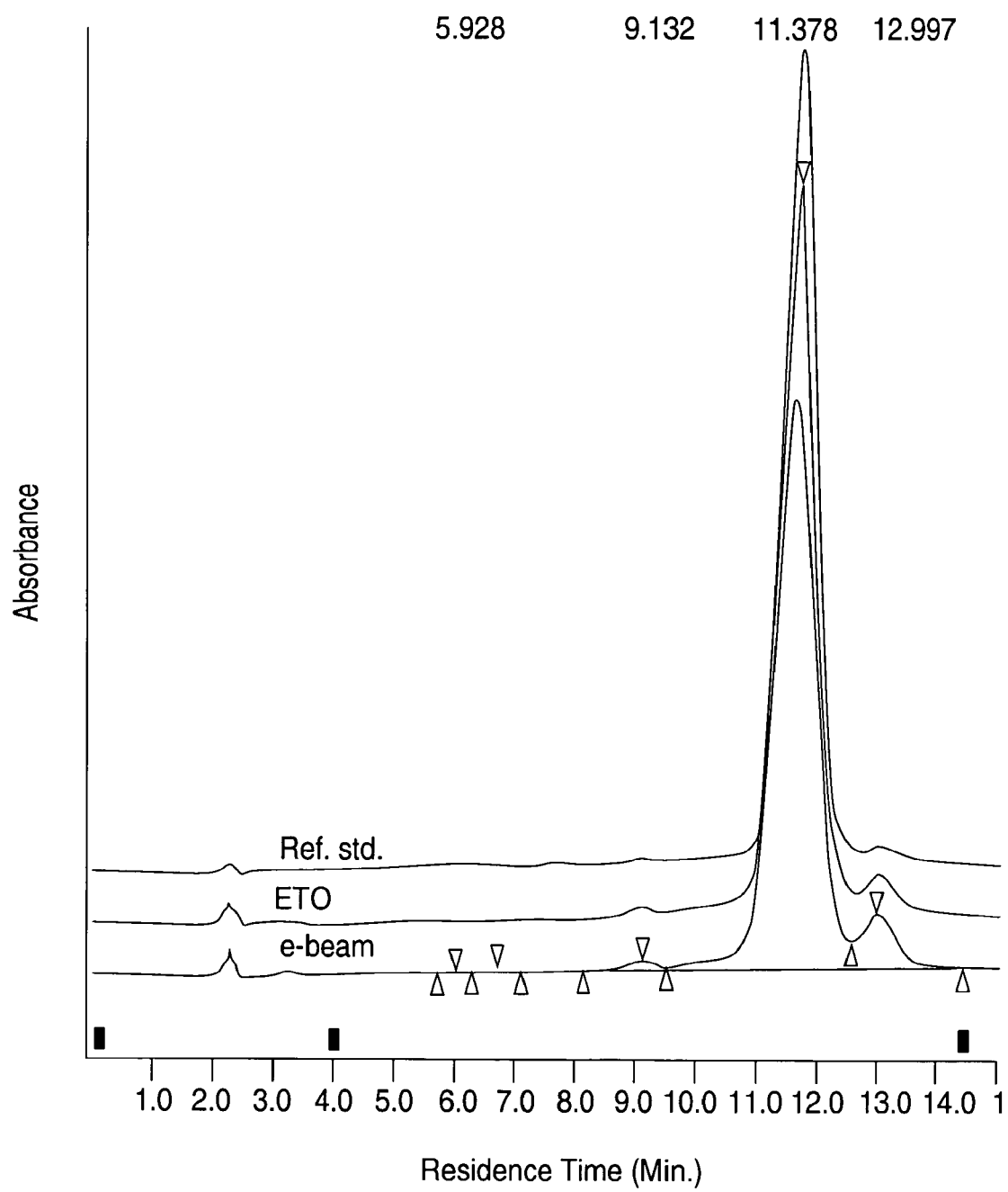
FIG. 8 is a chromatograph as referred to in Examples 32 and 33.

After sterilization, the coatings were then analyzed using an HPLC to determine the peak purity of the drug in the stent coatings. It was determined that the 40-O-(2-hydroxy)ethyl-rapamycin in the coatings had peak purities of about greater than 95%. FIG. 8 is a chromatograph showing the peak purity the 40-O-(2-hydroxy)ethyl-rapamycin in one of the coatings, labeled "ETO," as compared to a reference standard for 40-O-(2-hydroxy)ethyl-rapamycin, labeled "Ref. Std."

Example 33

Two stents were coated by spraying a 2% (w/w) solution of EVAL and 98% (w/w) dimethylacetamide to form a primer layer. For the primer layer, there was a target dry weight of 100 μg of polymer, and the measured dry weights were 99 μg and 94 μg, respectively. The two stents were then coated with an EVAL-40-O-(2-hydroxy)ethyl-rapamycin blend at a drug:polymer ratio of 2:1 to produce a reservoir layer. After application, it was determined that the reservoir layers had weights of 586 μg and 588 μg, respectively. From the total weight of the reservoir layers and the drug:polymer ratio, it was estimated that the coatings contained about 391 μg and 392 μg of 40-O-(2-hydroxy)ethyl-rapamycin, respectively. Polymeric barrier layers were also applied to the stents and it was determined that the weights of the barrier layers were 380 μg and 369 μg, respectfully.

The stents from this Example were then sterilized using an e-beam sterilization process. In particular, the stents were placed in a stent container which was run through an e-beam chamber. While moving through the e-beam chamber via a conveyor belt, the stent container was exposed to an e-beam with a constant energy level so that the stent container received between 33.11 and 46.24 KGy. The stent therefore at any point along the length of the stent received at a minimum 25 KGy.

After sterilization, the coating was then analyzed using an HPLC to determine the peak purity of the drug in the stent coating. It was determined that the 40-O-(2-hydroxy)ethyl-rapamycin in the coating had a peak purity of about greater than 95%. FIG. 8 is a chromatograph showing the peak purity the 40-O-(2-hydroxy)ethyl-rapamycin in one of the coatings, labeled "e-beam," as compared to a reference standard for 40-O-(2-hydroxy)ethyl-rapamycin, labeled "Ref. Std."

Example 34

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 44±3 μg of polymer. For the reservoir layer, the drug:polymer ratio was 1:2, and the measured average drug content was 245 μg as determined by Example 2. For the barrier layer, the measured average dry weight was 104 μg.

After the coatings were formed on the stents, a select number of stents were tested for the drug release rate from the coatings according to the procedure described in Example 18. It was determined that the average drug released in 24 hours was 23.5 μg, or 9.6% of the total.

Example 35

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 45±3 μg of polymer. For the reservoir layer, the drug:polymer ratio was 1:1.5, and the measured average drug content was 337 μg as determined by Example 2. For the barrier layer, the measured average dry weight was 169 μg.

After the coatings were formed on the stents, a select number of stents were tested for the drug release rate from the coatings according to the procedure described in Example 18. It was determined that the average drug released in 24 hours was 37.1 μg, or 11.0% of the total.

Example 36

Figure 9:
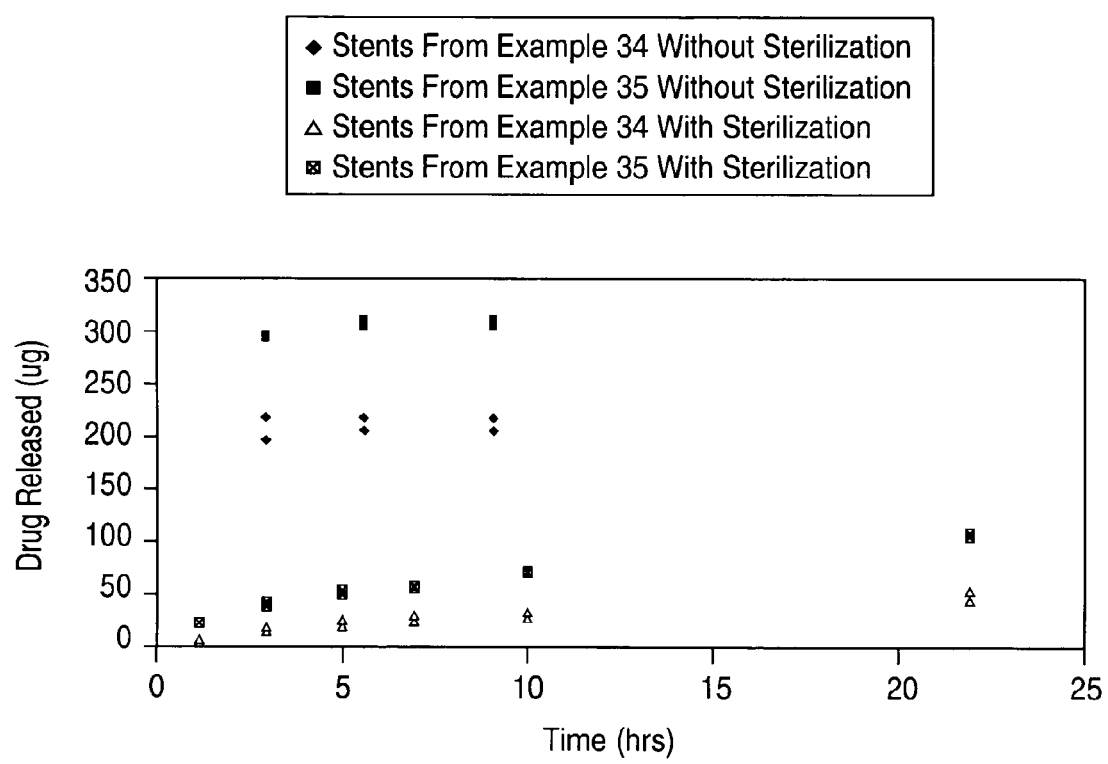
FIG. 9 is a graph showing the release rate of an active agent from stent coatings as referred to in Example 36.

Stents from Example 34 and stents from Example 35 were sterilized according to the process described in Example 32. The released rates of the drug in the stent coatings of sterilized stents and non-sterilized were then tested according to the process described in Example 5. The results of the release rate test are graphically shown in FIG. 9.

Example 37

A 13 mm PENTA stent can be coated by spraying a solution of EVAL, 40-O-(2-hydroxy)ethyl-rapamycin and ethanol onto the stent. The stent is then baked at 50° C. for 2 hours to yield a reservoir coating with 300 μg of EVAL and 300 μg of 40-O-(2-hydroxy)ethyl-rapamycin. A barrier layer can be formed by spraying the stent with a solution of EVAL and pentane. A second 2 hour bake at 50° C. can be performed to remove the solvent to yield a barrier coating with 320 μg of EVAL.

Example 38

A 13 mm PENTA stent can be coated by spraying a solution of EVAL and DMAC onto the stent. The solvent is removed by baking at 140° C. for 2 hours to yield a primer coating with 100 μg of EVAL. A reservoir layer can be applied by spraying a solution of EVAL, 40-O-(2-hydroxy)ethyl-rapamycin and ethanol onto the stent. The stent is then baked at 50° C. for 2 hours to yield a reservoir coating with 200 μg of EVAL and 400 μg of 40-O-(2-hydroxy)ethyl-rapamycin. A barrier layer can be formed by spraying the stent with a solution of EVAL and pentane. A second 2 hour bake at 50° C. is performed to remove the solvent to yield a barrier coating with 350 μg of EVAL.

Example 39

A 13 mm PENTA stent can be coated by spraying a solution of EVAL, 40-O-(2-hydroxy)ethyl-rapamycin and ethanol onto the stent. The stent is then baked at 50° C. for 2 hours to yield a reservoir coating with 500 μg of EVAL and 250 μg of 40-O-(2-hydroxy)ethyl-rapamycin. A barrier layer can be formed by spraying the stent with a solution of EVAL and pentane. A second 2 hour bake at 50° C. is performed to remove the solvent to yield a barrier coating with 300 μg of EVAL.

Example 40

A 13 mm PENTA stent can be coated by spraying a solution of EVAL, 40-O-(2-hydroxy)ethyl-rapamycin and ethanol onto the stent. The stent is then baked at 50° C. for 2 hours to yield a reservoir coating with 475 μg of EVAL and 175 μg of 40-O-(2-hydroxy)ethyl-rapamycin. A barrier layer can be formed by spraying the stent with a solution of EVAL and pentane. A second 2 hour bake at 50° C. is performed to remove the solvent to yield a barrier coating with 300 μg of EVAL.

Example 41

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 400 μg of EVAL and 200 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 300 μg of EVAL.

Example 42

An 8 mm Pixel stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 400 μg of EVAL and 200 μg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 150 μg of PBMA.

Example 43

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 μg of EVAL and 200 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 200 μg of EVAL.

Example 44

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 μg of EVAL and 200 μg of 40-O-(2-hydroxy)ethyl-rapamycin. A barrier layer can formed by spraying the stent with a solution of PBMA and HFE FLUX REMOVER. A second 2 hour bake at 50° C. is performed to remove the solvent to yield a barrier coating with 150 μg of PBMA.

Example 45

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 μg of EVAL and 200 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 200 μg of EVAL.

Example 46

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 μg of EVAL and 200 μg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 100 μg of PBMA.

Example 47

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 270 μg of EVAL and 150 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 150 μg of EVAL.

Example 48

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 170 μg of EVAL and 150 μg of 40-O-(2-hydroxy)ethyl-rapamycin. A barrier layer can be formed by spraying the stent with a solution of PBMA and HFE FLUX REMOVER. A second 2 hour bake at 50° C. is pertained to remove the solvent to yield a barrier coating with 75 μg of PBMA.

Example 49

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 150 μg of EVAL and 150 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 200 μg of EVAL. A finishing layer can then applied by spraying the stent with a solution of EVAL, polyethylene oxide (molecular weight of 17.5 K) ("PEO") and dimethylacetamide. The stent is baked at 50° C. for 2 hours to remove the solvent to yield a finishing coating with 83 μg of EVAL and 17 μg of PEO.

Example 50

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 270 μg of EVAL and 150 μg of 40-O-(2-hydroxy)ethyl-rapamycin. A barrier layer can formed by spraying the stent with a solution of EVAL and a mixture of dimethylacetamide and pentane. A second 2 hour bake at 50° C. is performed to remove the solvent to yield a barrier coating with 150 μg of EVAL. A finishing layer can then applied by spraying the stent with a solution of EVAL, PEO and dimethylacetamide. The stent is baked at 50° C. for 2 hours to remove the solvent to yield a finishing coating with 83 μg of EVAL and 17 μg of PEO.

Example 51

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 μg of EVAL and 200 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 100 μg of EVAL.

Example 52

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 μg of EVAL and 200 μg of 40-O-(2-hydroxy)ethyl-rapamycin. A barrier layer can be formed by spraying the stent with a solution of EVAL, KYNAR and HFE FLUX REMOVER. A second 2 hour bake at 50° C. is performed to remove the solvent to yield a barrier coating with 50 μg of EVAL and 50 μg of KYNAR.

Example 53

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 μg of EVAL and 200 μg of 40-O-(2-hydroxy)ethyl-rapamycin. A barrier layer is formed by spraying the stent with a solution of EVAL and a mixture of dimethylacetamide and pentane. A second 2 hour bake at 50° C. is performed to remove the solvent to yield a barrier coating with 200 μg of EVAL.

Example 54

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 μg of EVAL and 200 μg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 100 μg of PBMA.

Example 55

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 μg of EVAL and 200 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 200 µg of EVAL.

Example 56

An 8 mm PIXEL stent is coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 µg of EVAL and 200 µg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 100 µg of EVAL. A finishing layer can then be applied by spraying the stent with a solution of EVAL, PEO and dimethylacetamide. The stent is baked at 50° C. for 2 hours to remove the solvent to yield a finishing coating with 83 µg of EVAL and 17 µg of PEO.

Example 57

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 µg of EVAL and 200 µg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 75 µg of PBMA. A finishing layer can then be applied by spraying the stent with a solution of PBMA, PEO and dimethylacetamide. The stent is baked at 50° C. for 2 hours to remove the solvent to yield a finishing coating with 62.5 µg of PBMA and 12.5 µg of PEO.

Example 58

The purpose of this study was to evaluate 40-O-(2-hydroxy)ethyl-rapamycin in its ability to prevent excessive neointimal proliferation following stenting in a 28-day porcine coronary artery stent model. Specifically, two formulations of 40-O-2-hydroxy)ethyl-rapamycin and EVAL were coated onto Multi-Link Pent™ stents. These two formulations of drug eluting stents were compared to a polymer control and a bare stent control in terms of safety and efficacy in a 28 day in vivo porcine model.

The following are the materials used for this Example:
1. Experimental animals: Thirteen 30-45 kg Yorkshire cross pigs, male or female.
2. Stents: MULTI-LINK PENTA™ (3.0×13 mm) with the following coatings:
    Six Bare stainless steel stents (Control Group).
    Nine True Coat™ stents (EVAL Polymer Control Group) have 800 µg of EVAL.
    Nine stents having a reservoir layer with 40-O-(2-hydroxy)ethyl-rapamycin (205 µg of drug, with a drug to polymer ratio of 1:1.75) and a 189 µg EVAL topcoat.
    Nine stents having a reservoir layer with 40-O-(2-hydroxy)ethyl-rapamycin (282 µg of drug, with a drug to polymer ratio of 1:1.6) and a 130 µg EVAL topcoat.
3. BMW™ wires 0.014", 190 cm.
4. Guide wire 0.035", 190 cm.
5. Viking guide catheters, 7 F.
6. Introducer sheaths (8-10 F).
7. ACS 20/20 Indeflator™ Inflation Device.
8. Heparinized saline.
9. Nitroglycerin, Lidocaine, other inotropic/chronotropic drugs.
10. Standard surgical equipment, anesthetic, and medications as necessary.
11. Respiratory and hemodynamic monitoring systems.
12. Positive pressure ventilator and associated breathing circuits.
13. ACT machine and accessories.
14. PTCA accessories.
15. Ambulatory defibrillator.
16. Fluoroscopy equipment.
17. Non-ionic contrast agent.

Thirteen (13) pigs were evaluated in this study. Eleven (11) pigs were used for the 28-day chronic study in order to evaluate the vascular response to the drug eluting stents. Three stents were implanted in each animal. Stents were deployed in the right coronary artery (RCA), the left anterior descending artery (LAD), and the left circumflex coronary artery (LCX) for the 28-day duration. All stents were deployed at a 1.1:1 stent: artery ratio allowing slight to moderate injury in order to assess the drugs ability to prevent excessive neointimal proliferation following stenting. Each stented vessel underwent follow up angiography and histo-pathological evaluation in order to assess the chronic vascular cellular response and to assess if the drug has any effect in reducing neointimal proliferation compared to controls.

Pre-clinical animal testing was performed in accordance with the NIH Guide for the Care and Use of Laboratory Animals. The animals were housed at an animal facility. Animals were shipped off-site for chronic housing once fully recovered from the procedure. All animal care, husbandry, and veterinary issues fell under the responsibility of the institutional veterinarian.

All animals received aspirin (325 mg PO) and Ticlopidine (500 mg PO) once daily for three days prior to undergoing stent placement. All stent placement procedures were performed on anesthetized pigs using aseptic technique. A baseline angiogram was obtained and three target sites (1 per coronary vessel) were selected with 2.7-3.2 mm vessel diameter. Vessel size was determined by using the guiding catheter as a reference or with on line Quantitative Coronary Angiographic analysis (QCA). After selection of a target site, the appropriate products was prepared for use and stents were deployed in such a manner as to achieve a 1.1:1.0 overstretch of the vessel. After recovery from anesthesia, each pig was treated with Ticlopidine (500 mg PO) once daily for the duration of the study and Aspirin (325 mg PO) once daily for the duration of the study.

After 28 days each animal underwent a follow-up angiography in order to re-assess patency, deployment and placement of stents. Additionally, online QCA measurements were made to provide angiographic estimates of the minimal luminal diameters (MLD) and percentage of vessel lumen restenosis. All follow-up angiography procedures were performed on anesthetized pigs using clean technique. Aseptic technique was not necessary as this is an acute procedure.

The pigs were euthanized immediately following the follow-up angiography. The hearts were removed, perfused with saline and pressure perfusion fixed with formalin before being placed into a labeled container with formalin and submitted for pathological evaluation. Sections of the treated coronary arteries were sent to a contracted pathology site. Five cross sections of the stented vessel were prepared including one section of each vessel ends and three sections of the stented area. The tissue was stained with haemoatoxylin and eosin and with an elastin stain. A morphometric analysis of the stented arteries was performed which included an assessment of stent strut position and determination of vessel/lumen areas, percent stenosis, injury scores, intimal and medial areas and intima/media ratios.

The following is a list of the general procedure used for this Example:

A. Animal Preparation
1. Administer Aspirin (325 mg PO) and Ticlopidine (500 mg PO) once daily starting 3 days prior to stent implantation.
2. Sedate the pigs according to the institutional standard operating procedure.
3. Intubate the trachea via an oral approach.
4. Deliver isoflurane (up to 5%) to achieve and maintain an adequate plane of anesthesia.
5. Shave the sheath introduction area free of hair and scrub the surgical site with surgical soap and/or antiseptic solution.
6. Place a 8-10 F introducer sheath into the right or left femoral artery.
7. Obtain an arterial blood sample for a baseline ACT.
8. Record rectal temperature.
9. Administer heparin 200 units/kg IV (not to exceed 100,000 units) and obtain a blood sample for measurement of ACT 5-10 minutes later.
10. Repeat heparin as needed to maintain ACT ≧300 seconds.
11. Measure and record arterial blood pressure, heart rate and electrocardiogram (ECG).

B. Angiography for Vessel Selection
1. Advance the guiding catheter over the guidewire into the aortic arch and cannulate the desired vessel.
2. Administer nitroglycerin 200 µg intra-luminally prior to baseline angiography.
3. Perform baseline angiogram and record images on cine.
4. With the diameter of the guiding catheter as a reference, select vasculature that will allow a target stent to artery ratio of 1.1:1.0.

C. Stent Preparation and Deployment
1. Perform online QCA and measure baseline proximal, target, and distal reference sites.
2. Administer nitroglycerin (200 µg) intra-luminally prior to stent deployment, then as needed to control coronary artery vasospasm.
3. Inspect the stent delivery system. Ensure that the stent is correctly positioned on the balloon. Inspect the stent for any abnormalities.
4. Flush guidewire lumen with heparinized saline until fluid exits the guidewire notch.
5. Prepare Indeflator/syringe with diluted (approximately 50:50) contrast medium.
6. Attach syringe to test catheter inflation port; use standard techniques to fill the inflation lumen with diluted contrast.
7. Purge syringe and test catheter inflation lumen of all air.
8. Purge Indeflator of all air and attach to test catheter inflation port.
9. Position an appropriate guidewire in the distal bed of the target artery.
10. Insert the stent delivery system through the guiding catheter over the guidewire.
11. Advance the stent delivery system to the pre-selected arterial deployment site.
12. Position balloon for inflation.
13. Refer to IFU for inflation strategy. If no IFU available, inflate the balloon at a slow steady rate to a pressure that expands the stent to the desired diameter. Hold at this pressure for 30 seconds.
14. Record inflated balloon by pulling image on cine. Perform on-line QCA and measure the inflated balloon diameter.
15. Deflate balloon by pulling negative pressure. While withdrawing the system, observe tactually and fluoroscopically. Record any resistance.
16. Administer nitroglycerin (200 µg) intra-luminally.
17. Assess patency, deployment, and placement of stent via coronary angiography.
18. Assess TIMI angiographic low grade.
19. Record on cine and video.
20. Measure post-proximal, target, and distal MLD with QCA.
21. Repeat Section C with remaining stent delivery systems.
22. Measure and record heart rate, arterial blood pressure and electrocardiogram (ECG).

D. Stent Procedure End
1. Remove the guidewire, guiding catheter and introducer sheath.
2. Remove introducer sheath from the femoral artery.
3. Ligate the artery with 3-0 suture material at the side of sheath entry.
4. Appose the muscular and subcutaneous tissue layer using suture material.
5. Allow the animal to recover from anesthesia in an individual cage.
6. Give Buprenorphine (0.05 mg/kg) PRN as needed for pain.
7. Administer Ticlopidine (250 mg PO) and aspirin (325 mg PO) once daily until date of follow-up angiography.

E. Follow-up Angiography for 28-Day Study Pigs
1. Following an overnight fast, sedate the pigs according to the institutional standard operating procedure.
2. Intubate the trachea via an oral approach.
3. Deliver isoflurane at a concentration up to 5% as needed to maintain surgical plane of anesthesia.
4. Shave the cut-down area free of hair and scrub the surgical site with surgical soap and/or antiseptic solution.
5. Measure and record arterial blood pressure, heart rate and electrocardiogram (ECG).
6. Record animal number and study identification tag on cine.
7. Advance the guiding catheter over a guidewire to cannulate the ascending aorta to appropriate vessel.
8. Administer nitroglycerine (200 µg IC) prior to angiography.
9. Perform an angiogram. Record images on cine and video (if available).
10. Assess patency, deployment and placement of stents via angiography.
11. Obtain online QCA measurements to record the proximal and distal reference vessel diameters and the minimal luminal diameters (MLD).
12. Give TIMI scores.

F. Procedure End
1. Remove the guiding catheter and introducer sheath.
2. Euthanize the animal with an overdose of barbiturates and/or potassium chloride.
3. Remove the heart and all arteries containing the implanted stents.

4. Perfusion fix the heart and other implanted vessels by infusing 250 ml of Lactated Ringers solution or physiologic saline followed by approximately 0.5-1.0 liters of formalin under a pressure of approximately 100 mmHg.
5. Place heart into labeled container with formalin solution for gross and microscopic examination of heart and implanted vasculature.

The percent mean stenosis and percent mean neointimal area for the different groups were calculated. The following Table 11 demonstrates that both of the formulations of the drug eluting stents having 40-O-(2-hydroxy)ethyl-rapamycin significantly reduced the percent stenosis and percent mean neointimal area as compared to the control groups.

TABLE 11

| Treatment Group | Percent Mean Stenosis | Standard Deviation | Percent Mean Neointimal Area | Standard Deviation |
|---|---|---|---|---|
| Bare Stent | 29.54 | 14.86 | 2.37 | 1.06 |
| EVAL Control | 37.54 | 10.62 | 3.00 | 0.64 |
| Formulation 1 | 20.67 | 4.79 | 1.64 | 0.35 |
| Formulation 2 | 24.29 | 9.75 | 1.85 | 0.38 |

Example 59

13 mm PIXEL-D stents were coated by spraying a 2% (w/w) solution of EVAL and 98% (w/w) dimethylacetamide. The solvent was removed by baking at 140° C. for 2 hours. The target primer layer weight was 58.2 µg. For the reservoir layer, a solution of EVAL and actinomycin D in a mixture of 75% (w/w) dimethylacetamide and 25% (w/w) ethanol was spray coated onto the stents. The ratio of EVAL to actinomycin D was 9 to 1. The stents were then baked at 50° C. for 2 hours. The target weight for the reservoir layer was 90 µg. A barrier layer was formed by spraying the stents with a solution of EVAL in a mixture of 80% (w/w) dimethylacetamide and 20% (w/w) pentane. Another 2 hour bake at 50° C. was performed to remove the solvent. The target weight for the barrier layer was 218 µg.

After the solvent had been substantially removed and the coatings had been formed, a select number of stents were then subjected to a standard grip process in order to mount the stent onto a catheter. The stents were separated into four test groups. Group 1 served as the control group and were mounted at room temperature; Group 2 was exposed to a temperature of about 82.2° C. (180° F.) for about 2 minutes; Group 3 was exposed to a temperature of about 93.3° C. (200° F.) for about 2 minutes; and Group 4 was exposed to a temperature of about 121.1° C. (250° F.) for about 2 minutes.

Five stents from each group were tested to determine if the total content of the active agent was affected by the thermal treatment. The results demonstrated that the thermal treatment process did not affect the total content. The results for the total drug content test are shown in Table 12.

TABLE 12

| | Mean Total Content (µg) | Standard Deviation (µg) |
|---|---|---|
| Control | 104 | 3.4 |
| Group 1 (82.2° C.) | 105 | 10.1 |

TABLE 12-continued

| | Mean Total Content (µg) | Standard Deviation (µg) |
|---|---|---|
| Group 2 (93.3° C.) | 105 | 7.2 |
| Group 3 (121.1° C.) | 107 | 2.7 |

Ten stents from each group were then tested to determine the release rate of the active agent in a 24 hour period. The results demonstrated that the thermal treatment process decreased the mean release rate for a 24 hour period. Additionally, the thermal treatment process decreased the standard deviation. The results for the release rate test are shown in Table 13.

TABLE 13

| | Mean Release Rate (µg/24 hours) | Standard Deviation (µg) |
|---|---|---|
| Control | 33.1 | 12.4 |
| Group 1 (82.2° C.) | 28.5 | 7.3 |
| Group 2 (93.3° C.) | 19.2 | 9.6 |
| Group 3 (121.1° C.) | 21.9 | 4.0 |

Example 60

13 mm PIXEL-D stents were coated by spraying a 2% (w/w) solution of EVAL and 98% (w/w) dimethylacetamide. The solvent was removed by baking at 140° C. for 2 hours. The target primer layer weight was 40 µg. For the reservoir layer, a solution of EVAL and actinomycin D in a mixture of 75% (w/w) dimethylacetamide and 25% (w/w) ethanol was spray coated onto the stents. The ratio of EVAL to actinomycin D was 9 to 1, and a target total dose of 7.9 µg. The stents were then baked at 50° C. for 2 hours. The target weight for the reservoir layer was 79 µg. A barrier layer was formed by spraying the stents with a solution of EVAL in a mixture of 80% (w/w) dimethylacetamide and 20% (w/w) pentane. Another 2 hour bake at 50° C. was performed to remove the solvent. The target weight for the barrier layer was 135 µg.

After the solvent had been substantially removed and the coatings had been formed, a select number of stents were then subjected to different thermal treatment processes. One process included subjecting stents to a two hour thermal treatment before the mounting process. In particular, a select number of coated stents were placed in a convection oven and subjected to a temperature of about 80° C. for about 2 hours. The other process included subjecting stents to a two minute thermal treatment during the mounting procedure. In particular, Group 1 was the control group and was mounted at room temperature; Group 2 was exposed to a temperature of about 82.2° C. (180° F.) for about 2 minutes; and Group 3 was exposed to a temperature of about 121.1° C. (250° F.) for about 2 minutes. Table 14 shows the number of stents used in each of the test groups.

TABLE 14

| Temperature during Stent Mounting Process | Two Hour Thermal Treatment Process | Without Two Hour Thermal Treatment Process |
|---|---|---|
| Control (Room Temperature) | 10 | 10 |
| Group 1 (82.2° C.) | 10 | 10 |
| Group 2 (121.1° C.) | 15 | 15 |

Stents from Group 2, including stents from the two hour treatment group and the non-two hour treatment group, were tested to determine if the total content of the active agent was affected by the two hour thermal treatment process. The results demonstrated that the thermal treatment process did not affect the total content. In particular, the average total content for the stents that were subjected to the two hour treatment was 9.3 µg/cm²±0.6, whereas the average total content for the stents that were not subjected to the two hour treatment was 8.8 µg/cm²±0.6.

A select number of stents from each group were then tested to determine the release rate of the active agent in a 24 hour period. The results demonstrated that both thermal treatment processes decreased the mean release rate for a 24 hour period. The results for the release rate tests are shown in Table 15.

TABLE 15

| | Mean Release Rate (µg/24 hours) and Standard Deviation | |
|---|---|---|
| Temperature during Stent Mounting Process | Two Hour Thermal Treatment Process | Without Two Hour Thermal Treatment Process |
| Control (Room Temperature) | 17.8 ± 4.8 | 37.0 ± 11.2 |
| Group 1 (82.2° C.) | 21.2 ± 9.0 | 28.1 ± 9.0 |
| Group 2 (121.1° C.) | 9.0 ± 2.7 | 10.2 ± 1.9 |

Example 61

13 mm PIXEL-D stents were coated by spraying a 2% (w/w) solution of EVAL and 98% (w/w) dimethylacetamide. The solvent was removed by baking at 140° C. for 2 hours. For the reservoir layer, a solution of EVAL and actinomycin D in a mixture of 75% (w/w) dimethylacetamide and 25% (w/w) ethanol was spray coated onto the stents. The ratio of EVAL to actinomycin D was 9 to 1. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

After the solvent had been substantially removed and the coatings had been formed, the stents were then subjected to various thermal treatment and storage conditions. In particular, test groups were subjected to different conditions to study the effect of (1) exposure temperatures (40° C., 50° C. or 80° C.); (2) exposure time (2 or 7 hours); and (3) storage time (0 or 30 days). Table 16 summarizes the different test parameters.

TABLE 16

| Group | Exposure Temperature (° C.) | Exposure Time (Hours) | Storage Time at 25° C. (Days) |
|---|---|---|---|
| A0 | Room Temperature | N/A | 0 |
| A1 | 40 | 2 | 0 |
| A2 | 40 | 7 | 0 |
| A3 | 50 | 2 | 0 |
| A4 | 50 | 7 | 0 |
| A5 | 80 | 2 | 0 |
| A6 | 80 | 7 | 0 |
| B1 | 50 | 2 | 30 |
| B2 | 50 | 7 | 30 |
| B3 | 80 | 2 | 30 |
| B4 | 80 | 7 | 30 |

After the stents were exposed to the thermal treatment, the stents were sterilized using an e-beam process. During the e-beam process, the stents were exposed to 35 kGy of radiation using a one pass process.

Five stents from each group were tested to determine if the total content of the active agent was affected by the thermal treatment. Ten stents from each group were then tested to determine the release rate of the active agent in a 24 hour period. The results demonstrated that the thermal treatment process did not affect the total content. The results also demonstrated that the thermal treatment process decreased the mean release rate for a 24 hour period. The results for the total content and release rate test are shown in Table 17.

TABLE 17

| Group | Exposure Temperature (° C.) | Exposure Time (hours) | Storage Time at 25° C. (Days) | Release Rate (%/24 hours) | Total Content (% of target concentration) |
|---|---|---|---|---|---|
| A0 | Control | | | 16.2 ± 2.0 | 91.2 ± 1.9 |
| A1 | 40 | 2 | 0 | 14.9 ± 4.6 | 96.6 ± 5.5 |
| A2 | 40 | 7 | 0 | 15.0 ± 6.0 | 83.6 ± 6.9 |
| A3 | 50 | 2 | 0 | 15.5 ± 3.4 | 89.2 ± 8.2 |
| A4 | 50 | 7 | 0 | 19.3 ± 4.1 | 87.2 ± 6.1 |
| A5 | 80 | 2 | 0 | 9.1 ± 2.9 | 87.7 ± 12.8 |
| A6 | 80 | 7 | 0 | 7.6 ± 1.1 | 96.9 ± 8.7 |
| B1 | 50 | 2 | 30 | 20.4 ± 3.0 | 94.4 ± 8.3 |
| B2 | 50 | 7 | 30 | 19.7 ± 4.2 | 87.6 ± 2.3 |
| B3 | 80 | 2 | 30 | 11.5 ± 1.8 | 78.7 ± 8.0 |
| B4 | 80 | 7 | 30 | 10.1 ± 2.2 | 89.9 ± 3.5 |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of manufacturing a drug delivery stent, the method comprising:
   forming a dry polymeric coating on a stent having less than about 2% residual fluid content (w/w), the dry polymeric coating comprising a reservoir layer comprising a polymer and an active agent, and a barrier layer comprising a polymer covering a portion of the reservoir layer; and
   subjecting the polymer of the barrier layer to a heat treatment at a temperature equal to or greater than the glass transition of the polymer of the barrier layer;
   wherein the polymer of the barrier layer comprises an ethylene vinyl alcohol copolymer, an ethylene-vinyl acetate copolymer, poly(butylmethacrylate), or a combination thereof.

2. The method of claim 1, wherein the active agent is rapamycin, 40-O-(2-hydroxy)ethyl-rapamycin, or a functional analog or structural derivative thereof.

3. The method of claim 1, wherein the glass transition temperature of the polymer of the barrier layer is greater than the glass transition temperature of the polymer of the reservoir layer.

4. The method of claim 1, wherein the glass transition temperature of the polymer of the barrier layer is lower than the glass transition temperature of the polymer of the reservoir layer.

5. The method of claim 1, wherein the glass transition temperature of the polymer of the barrier layer is about the same as the glass transition temperature of the polymer of the reservoir layer.

6. The method of claim 1, wherein the temperature of the heat treatment is less than the melting temperature of the polymer of the barrier layer.

7. The method of claim 1, wherein the temperature of the heat treatment is less than the melting temperature of the polymer of the reservoir layer.

8. The method of claim 1, wherein the temperature of the heat treatment is equal to the glass transition temperature of the polymer of the barrier layer plus the melting temperature of the polymer of the barrier layer, divided by 2.

9. The method of claim 1, wherein the temperature of the heat treatment is equal to 0.9 times the melting temperature of the polymer of the barrier layer, wherein the melting temperature of the polymer of the barrier layer is expressed in Kelvin.

10. The method of claim 1, wherein the glass transition temperature of the polymer of the barrier layer is above room temperature.

11. A method of manufacturing a drug delivery stent, the method comprising:
    forming a polymeric coating on a stent, the polymeric coating comprising a reservoir layer comprising a polymer and an active agent, and a barrier layer comprising a semicrystalline polymer covering a portion of the reservoir layer; and
    exposing the polymer of the barrier layer to the crystallization temperature of The polymer of the barrier layer.

12. The method of claim 11, wherein the polymeric coating comprises less than about 2% residual fluid content (w/w).

13. The method of claim 11, wherein the active agent is rapamycin, 40-O-(2-hydroxy)ethyl-rapamycin, or a functional analog or structural derivative thereof.

14. The method of claim 11, wherein the polymer of the reservoir layer is a semicrystalline polymer and wherein the crystallization temperature of the polymer of the barrier layer is greater than the crystallization temperature of the polymer of the reservoir layer.

15. The method of claim 11 wherein the polymer of the reservoir layer is a semicrystalline polymer and wherein the crystallization temperature of the polymer of the barrier layer is less than the crystallization temperature of the polymer of the reservoir layer.

16. The method of claim 11, wherein the polymer of the reservoir layer is a semicrystalline polymer and wherein the crystallization temperature of the polymer of the barrier layer is equal to the crystallization temperature of the polymer of the reservoir layer.

17. A method of manufacturing a drug delivery stent, the method comprising:
    forming a dry polymeric coating on a stent having less than about 2% residual fluid content (w/w), the dry polymeric coating comprising a reservoir layer comprising a polymer and an active agent, and a barrier layer comprising a polymer covering a portion of the reservoir layer; and
    subjecting the polymer of the barrier layer to a heat treatment at a temperature equal to or greater than the glass transition of the polymer of the barrier layer;
    wherein the glass transition temperature of the polymer of the barrier layer is greater than the glass transition temperature of the polymer of the reservoir layer.

18. A method of manufacturing a drug delivery stent, the method comprising:
    forming a dry polymeric coating on a stent having less than about 2% residual fluid content (w/w), the dry polymeric coating comprising a reservoir layer comprising a polymer and an active agent, and a barrier layer comprising a polymer covering a portion of the reservoir layer; and
    subjecting the polymer of the barrier layer to a heat treatment at a temperature equal to or greater than the glass transition of the polymer of the barrier layer;
    wherein the glass transition temperature of the polymer of the barrier layer is lower than the glass transition temperature of the polymer of the reservoir layer.

19. A method of manufacturing a drug delivery stent, the method comprising:
    forming a dry polymeric coating on a stent having less than about 2% residual fluid content (w/w), the dry polymeric coating comprising a reservoir layer comprising a polymer and an active agent, and a barrier layer comprising a polymer covering a portion of the reservoir layer; and
    subjecting the polymer of the barrier layer to a heat treatment at a temperature equal to or greater than the glass transition of the polymer of the barrier layer;
    wherein the temperature is equal to 0.9 times the melting temperature of the polymer of the barrier layer, wherein the melting temperature of the polymer of the barrier layer is expressed in Kelvin.

\* \* \* \* \*